(12) United States Patent
Bertagnolli et al.

(10) Patent No.: US 8,158,258 B2
(45) Date of Patent: Apr. 17, 2012

(54) POLYCRYSTALLINE DIAMOND

(75) Inventors: Kenneth E. Bertagnolli, Riverton, UT (US); Jiang Qian, Cedar Hills, UT (US); Jason Wiggins, Draper, UT (US); Michael Vail, Genola, UT (US)

(73) Assignee: US Synthetic Corporation, Orem, UT (US)

( * ) Notice: Subject to any disclaimer, the term of this patent is extended or adjusted under 35 U.S.C. 154(b) by 0 days.

(21) Appl. No.: 12/846,604

(22) Filed: Jul. 29, 2010

(65) Prior Publication Data
US 2010/0310855 A1 Dec. 9, 2010

Related U.S. Application Data

(62) Division of application No. 12/244,960, filed on Oct. 3, 2008, now Pat. No. 7,866,418.

(51) Int. Cl.
*B32B 9/00* (2006.01)
(52) U.S. Cl. .................................. 428/408; 428/325
(58) Field of Classification Search .................. 428/325, 428/408
See application file for complete search history.

(56) References Cited

U.S. PATENT DOCUMENTS

| | | | |
|---|---|---|---|
| 3,101,260 A | 8/1963 | Cheney | |
| 3,141,746 A | 7/1964 | De Lai | |
| 3,574,580 A | 4/1971 | Stromberg et al. | |
| 4,425,315 A | 1/1984 | Tsuji et al. | |
| 4,610,600 A | 9/1986 | Bleier | |
| 4,610,699 A | 9/1986 | Yazu et al. | |
| 4,636,253 A | 1/1987 | Nakai et al. | |
| 5,355,969 A | 10/1994 | Hardy et al. | |
| 5,769,176 A | 6/1998 | Sumiya et al. | |
| 5,875,862 A | 3/1999 | Jurewicz et al. | |
| 5,889,219 A | 3/1999 | Moriguchi et al. | |
| 6,090,343 A | 7/2000 | Kear et al. | |
| 6,132,675 A | 10/2000 | Corrigan et al. | |
| 6,338,754 B1 | 1/2002 | Cannon et al. | |
| 6,342,301 B1 | 1/2002 | Yoshida et al. | |
| 6,655,234 B2 | 12/2003 | Scott | |
| 6,913,633 B2 | 7/2005 | Fries et al. | |
| 6,987,318 B2 | 1/2006 | Sung | |
| 7,108,598 B1 | 9/2006 | Galloway | |
| 7,493,972 B1 | 2/2009 | Schmidt et al. | |

(Continued)

FOREIGN PATENT DOCUMENTS

EP 0462955 12/1991

(Continued)

OTHER PUBLICATIONS

U.S. Appl. No. 12/244,960, filed Sep. 27, 2010, Notice of Allowance.

(Continued)

*Primary Examiner* — Archene Turner
(74) *Attorney, Agent, or Firm* — Workman Nydegger

(57) ABSTRACT

Embodiments of the invention relate to polycrystalline diamond ("PCD") exhibiting enhanced diamond-to-diamond bonding. In an embodiment, PCD includes a plurality of diamond grains defining a plurality of interstitial regions. A metal-solvent catalyst occupies at least a portion of the plurality of interstitial regions. The plurality of diamond grains and the metal-solvent catalyst collectively exhibit a coercivity of about 115 Oersteads ("Oe") or more and a specific magnetic saturation of about 15 Gauss·cm³/grams ("G·cm³/g") or less. Other embodiments are directed to polycrystalline diamond compacts ("PDCs") employing such PCD, methods of forming PCD and PDCs, and various applications for such PCD and PDCs in rotary drill bits, bearing apparatuses, and wire-drawing dies.

62 Claims, 10 Drawing Sheets

U.S. PATENT DOCUMENTS

| | | | |
|---|---|---|---|
| 7,516,804 B2* | 4/2009 | Vail | 175/434 |
| 7,575,805 B2 | 8/2009 | Achilles et al. | |
| 7,628,234 B2 | 12/2009 | Middlemiss | |
| 2004/0140132 A1 | 7/2004 | Middlemiss | |
| 2005/0050801 A1 | 3/2005 | Cho et al. | |
| 2005/0139397 A1 | 6/2005 | Achilles et al. | |
| 2005/0210755 A1* | 9/2005 | Cho et al. | 428/408 |
| 2005/0262774 A1 | 12/2005 | Eyre et al. | |
| 2006/0162969 A1 | 7/2006 | Belnap et al. | |
| 2007/0014965 A1 | 1/2007 | Chodelka et al. | |
| 2008/0022806 A1 | 1/2008 | Sumiya | |
| 2008/0023231 A1 | 1/2008 | Vail | |
| 2008/0115424 A1 | 5/2008 | Can et al. | |
| 2008/0142276 A1 | 6/2008 | Griffo et al. | |
| 2008/0302579 A1 | 12/2008 | Keshavan et al. | |
| 2009/0152018 A1 | 6/2009 | Sani | |
| 2009/0208301 A1 | 8/2009 | Kuroda et al. | |
| 2010/0084196 A1 | 4/2010 | Bertagnolli et al. | |
| 2010/0112332 A1 | 5/2010 | Kuroda et al. | |
| 2010/0186304 A1 | 7/2010 | Burgess et al. | |
| 2010/0307069 A1 | 12/2010 | Bertagnolli et al. | |
| 2010/0307070 A1 | 12/2010 | Bertagnolli et al. | |
| 2011/0189468 A1 | 8/2011 | Bertagnolli et al. | |

FOREIGN PATENT DOCUMENTS

| | | |
|---|---|---|
| JP | 121251 | 6/1985 |
| WO | WO2004/106004 | 12/2004 |
| WO | WO2006/099194 | 9/2006 |
| WO | WO2007/020518 | 2/2007 |

OTHER PUBLICATIONS

U.S. Appl. No. 12/244,960, filed Nov. 29, 2010, Notice of Allowance.
U.S. Appl. No. 12/244,960, filed Dec. 22, 2010, Issue Notification.
U.S. Appl. No. 12/858,949, filed Dec. 23, 2010, Office Action.
Akashi et al; "Synthetis of Sintered Diamond with High Electrical Resistivity and Hardness"; J.Am. Ceram. Soc.; vol. 70, No. 10; 1987; pp. C-237-X-239.
Bochechka et al; "The Study of HP-HT Interaction between Co-Base Melts and Diamond Powders"; High Pressure Chemical Engineering; 1996; p. 457.
Ekimov et al.; "Sintering of a Nanodiamond in the Presence of Cobalt"; Inorganic Materials; vol. 45, No. 5; 2009; pp. 491-494.
Godick; "Message from Neil B. Godick"; PHLburg Technologies, Inc.; Oct. 2008.
Osipov et al; "A contribution to the study of the diamond solid state sintering."; Ceramica; vol. 49; 2003; pp. 151-157.
Shige et al; "Sintering of Diamond Powder Electroless-Plated with Co Metal", Science and Technology of New Diamond, pp. 251-255 (1990).
Tardim; "A Novel Method for Obtaining Polycrystalline Diamond Cutters"; Materials Science Forum; vols. 660-661; 2010; pp. 477-482.
International Search Report and Written Opinion from International Application PCT/US2010/059619.
U.S. Appl. No. 12/244,960, filed Oct. 3, 2008, Bertganolli, et al.
U.S. Appl. No. 12/690,998, filed Jan. 21, 2010, Bertganolli, et al.
U.S. Appl. No. 11/545,929, filed Oct. 10, 2006, Bertganolli, et al.
U.S. Appl. No. 12/785,014, filed May 21, 2010, Bertganolli, et al.
D.L. Decker, W.A. Basset, L. Merrill, H.T. Hall, and J.D. Barnett; "High-Pressure Calibration A Critical Review", J. Phys. Chem. Ref. Data, vol. 1, No. 3 (1972).
ASTM B887-03 (2008) "Standard Test Method for Determination of Coercivity (Hcs) of Cemented Carbides".
ASTM B886-03 (2008), "Standard Test Method for Determination of Magnetic Saturation (Ms) of Cemented Carbides".
W. Utsumi, N. Toyama, S. Endo, and F.E. Fujita, "X-ray diffraction under ultrahigh pressure generated with sintered diamond anvils", J. Appl. Phys., 60, 2201 (1986).
G. Rousse, S. Klotz, A.M. Saitta, J. Rodriguez-Carvajal, M.I. McMahon, B. Couzinet, and M. Mezouar, "Structure of the Intermediate Phase of PbTe at High Pressure", Physical Review B: Condensed Matter and Materials Physics, 71, 224116 (2005).
Tze-Pin Lin, Michael Hood, George A. Cooper, and Redd H. Smith, Residual Stresses in Polycrystalline Diamond Compacts, J. Am. Ceram. Soc. 77[6] pp. 1562-1568 (1994).
DR Moyle, ER Kimmel "Utilization of magnetic saturation measurements for carbon control in cemented carbides" Dec. 1984, American Society of Metals Metals/Materials Technology series 1984 ASM/SCTE conference on technology advancements in cemented carbide production 8415-009.
International Search Report and Written Opinion mailed Feb. 2, 2010 as issued in PCT/US2009/054398 filed Aug. 20, 2009.
U.S. Appl. No. 12/244,960, mail date Apr. 27, 2010, Restriction Requirement.
U.S. Appl. No. 12/244,960, mail date Jun. 16, 2010, Office Action.
U.S. Appl. No. 12/858,906, filed Aug. 18, 2010, Bertagnolli, et al.
U.S. Appl. No. 12/858,949, filed Aug. 18, 2010, Bertagnolli, et al.
German; "Particle Packing Characteristics", Metal Powder Industries Federation; pp. 101-103; 1989 (6 pages).
U.S. Appl. No. 12/244,960, mail date Nov. 29, 2010, Notice of Allowance.
U.S. Appl. No. 12/858,949, mail date Jun. 8, 2011, Office Action.
U.S. Appl. No. 12/858,949, mail date Jul. 28, 2011, Notice of Allowance.
U.S. Appl. No. 12/858,949, mail date Aug. 31, 2011, Issue Notification.
U.S. Appl. No. 12/690,998, mailed Feb. 27, 2012, Office Action.

* cited by examiner

POLYCRYSTALLINE DIAMOND

CROSS-REFERENCE TO RELATED APPLICATIONS

This application is a divisional of U.S. patent application Ser. No. 12/244,960 filed on 3 Oct. 2008, the disclosure of which is incorporated herein, in its entirety, by this reference.

BACKGROUND

Wear-resistant, superabrasive compacts are utilized in a variety of mechanical applications. For example, polycrystalline diamond compacts ("PDCs") are used in drilling tools (e.g., cutting elements, gage trimmers, etc.), machining equipment, bearing apparatuses, wire-drawing machinery, and in other mechanical apparatuses.

PDCs have found particular utility as superabrasive cutting elements in rotary drill bits, such as roller-cone drill bits and fixed-cutter drill bits. A PDC cutting element typically includes a superabrasive diamond layer commonly referred to as a diamond table. The diamond table may be formed and bonded to a substrate using a high-pressure, high-temperature ("HPHT") process. The PDC cutting element may also be brazed directly into a preformed pocket, socket, or other receptacle formed in the bit body. The substrate may often be brazed or otherwise joined to an attachment member, such as a cylindrical backing. A rotary drill bit typically includes a number of PDC cutting elements affixed to the bit body. It is also known that a stud carrying the PDC may be used as a PDC cutting element when mounted to a bit body of a rotary drill bit by press-fitting, brazing, or otherwise securing the stud into a receptacle formed in the bit body.

Conventional PDCs are normally fabricated by placing a cemented carbide substrate into a container with a volume of diamond particles positioned adjacent to the cemented carbide substrate. A number of such cartridges may be loaded into an HPHT press. The substrates and volume of diamond particles are then processed under HPHT conditions in the presence of a catalyst material that causes the diamond particles to bond to one another to form a matrix of bonded diamond grains defining a polycrystalline diamond ("PCD") table that is bonded to the substrate. The catalyst material is often a metal-solvent catalyst (e.g., cobalt, nickel, iron, or alloys thereof) that is used for promoting intergrowth of the diamond particles.

In one conventional approach, a constituent of the cemented carbide substrate, such as cobalt from a cobalt-cemented tungsten carbide substrate, liquefies and sweeps from a region adjacent to the volume of diamond particles into interstitial regions between the diamond particles during the HPHT process. The cobalt acts as a catalyst to promote intergrowth between the diamond particles, which results in formation of bonded diamond grains. Often, a solvent catalyst may be mixed with the diamond particles prior to subjecting the diamond particles and substrate to the HPHT process.

The presence of the solvent catalyst in the PCD table is believed to reduce the thermal stability of the PCD table at elevated temperatures. For example, the difference in thermal expansion coefficient between the diamond grains and the solvent catalyst is believed to lead to chipping or cracking of the PCD table during drilling or cutting operations, which can degrade the mechanical properties of the PCD table or cause failure. Additionally, some of the diamond grains can undergo a chemical breakdown or back-conversion to graphite via interaction with the solvent catalyst. At elevated high temperatures, portions of the diamond grains may transform to carbon monoxide, carbon dioxide, graphite, or combinations thereof, thus degrading the mechanical properties of the PDC.

One conventional approach for improving the thermal stability of a PDC is to at least partially remove the solvent catalyst from the PCD table of the PDC by acid leaching. However, removing the solvent catalyst from the PCD table can be relatively time consuming for high-volume manufacturing. Additionally, depleting the solvent catalyst may decrease the mechanical strength of the PCD table.

Despite the availability of a number of different PCD materials, manufacturers and users of PCD materials continue to seek PCD materials that exhibit improved mechanical and/or thermal properties.

SUMMARY

Embodiments of the invention relate to PCD exhibiting enhanced diamond-to-diamond bonding. In an embodiment, PCD includes a plurality of diamond grains defining a plurality of interstitial regions. A metal-solvent catalyst occupies the plurality of interstitial regions. The plurality of diamond grains and the metal-solvent catalyst collectively may exhibit a coercivity of about 115 Oersteds ("Oe") or more and a specific magnetic saturation of about 15 Gauss·cm$^3$/grams ("G·cm$^3$/g") or less.

In an embodiment, PCD includes a plurality of diamond grains defining a plurality of interstitial regions. A metal-solvent catalyst occupies the plurality of interstitial regions. The plurality of diamond grains and the metal-solvent catalyst collectively may exhibit a specific magnetic saturation of about 15 G·cm$^3$/g or less. The plurality of diamond grains and the metal-solvent catalyst define a volume of at least about 0.050 cm$^3$.

In an embodiment, a PDC includes a PCD table bonded to a substrate. At least a portion of the PCD table may comprise any of the PCD embodiments disclosed herein.

In an embodiment, a method includes enclosing a plurality of diamond particles that exhibit an average particle size of about 30 µm or less and a metal-solvent catalyst in a pressure transmitting medium to form a cell assembly. The method further includes subjecting the cell assembly to a temperature of at least about 1000° C. and a pressure in the pressure transmitting medium of at least about 7.5 GPa to form PCD.

Further embodiments relate to applications utilizing the disclosed PCD and PDCs in various articles and apparatuses, such as rotary drill bits, bearing apparatuses, wire-drawing dies, machining equipment, and other articles and apparatuses.

BRIEF DESCRIPTION OF THE DRAWINGS

The drawings illustrate several embodiments of the invention, wherein identical reference numerals refer to identical elements or features in different views or embodiments shown in the drawings.

DETAILED DESCRIPTION

Figure 1A:
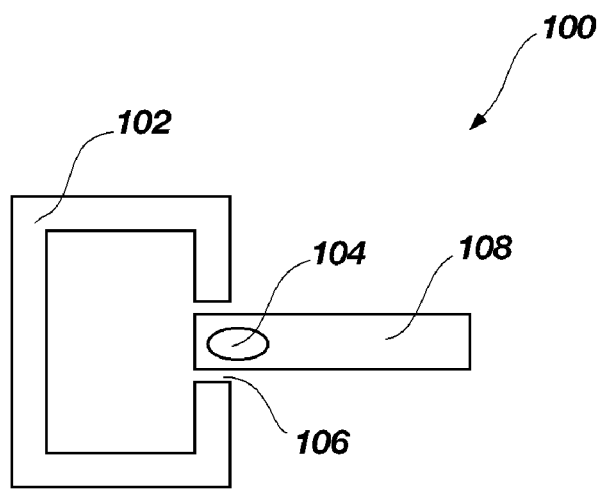
FIG. 1A is a schematic diagram of an example of a magnetic saturation apparatus configured to magnetize a PCD sample approximately to saturation.

Embodiments of the invention relate to PCD that exhibits enhanced diamond-to-diamond bonding. It is currently believed by the inventors that as the sintering pressure employed during the HPHT process used to fabricate such PCD is moved further into the diamond-stable region away from the graphite-diamond equilibrium line, the rate of nucleation and growth of diamond increases. Such increased nucleation and growth of diamond between diamond particles (for a given diamond particle formulation) may result in PCD being formed exhibiting a relatively lower metal-solvent catalyst content, a higher coercivity, a lower specific magnetic saturation, and/or a lower specific permeability (i.e., the ratio of specific magnetic saturation to coercivity) than PCD formed at a lower sintering pressure. Embodiments also relate to PDCs having a PCD table comprising such PCD, methods of fabricating such PCD and PDCs, and applications for such PCD and PDCs in rotary drill bits, bearing apparatuses, wire-drawing dies, machining equipment, and other articles and apparatuses.

PCD Embodiments

According to various embodiments, PCD sintered at a pressure of at least about 7.5 GPa may exhibit a coercivity of 115 Oe or more, a high-degree of diamond-to-diamond bonding, a specific magnetic saturation of about 15 G·cm$^3$/g or less, and a metal-solvent catalyst content of about 7.5 weight % ("wt %") or less. The PCD includes a plurality of diamond grains directly bonded together via diamond-to-diamond bonding to define a plurality of interstitial regions. At least a portion of the interstitial regions or, in some embodiments, substantially all of the interstitial regions may be occupied by a metal-solvent catalyst, such as iron, nickel, cobalt, or alloys of any of the foregoing metals. For example, the metal-solvent catalyst may be a cobalt-based material including at least 50 wt % cobalt, such as a cobalt alloy.

The diamond grains may exhibit an average grain size of about 50 μm or less, such as about 30 μm or less or about 20 μm or less. For example, the average grain size of the diamond grains may be about 10 μm to about 18 μm and, in some embodiments, about 15 μm to about 18 μm. In some embodiments, the average grain size of the diamond grains may be about 10 μm or less, such as about 2 μm to about 5 μm or submicron. The diamond grain size distribution of the diamond grains may exhibit a single mode, or may be a bimodal or greater grain size distribution.

The metal-solvent catalyst that occupies the interstitial regions may be present in the PCD in an amount of about 7.5 wt % or less. In some embodiments, the metal-solvent catalyst may be present in the PCD in an amount of about 3 wt % to about 7.5 wt %, such as about 3 wt % to about 6 wt %. In other embodiments, the metal-solvent catalyst content may be present in the PCD in an amount less than about 3 wt %, such as about 1 wt % to about 3 wt % or a residual amount to about 1 wt %. By maintaining the metal-solvent catalyst content below about 7.5 wt %, the PCD may exhibit a desirable level of thermal stability suitable for subterranean drilling applications.

Many physical characteristics of the PCD may be determined by measuring certain magnetic properties of the PCD because the metal-solvent catalyst may be ferromagnetic. The amount of the metal-solvent catalyst present in the PCD may be correlated with the measured specific magnetic saturation of the PCD. A relatively larger specific magnetic saturation indicates relatively more metal-solvent catalyst in the PCD.

The mean free path between neighboring diamond grains of the PCD may be correlated with the measured coercivity of the PCD. A relatively large coercivity indicates a relatively smaller mean free path. The mean free path is representative of the average distance between neighboring diamond grains of the PCD, and thus may be indicative of the extent of diamond-to-diamond bonding in the PCD. A relatively smaller mean free path, in well-sintered PCD, may indicate relatively more diamond-to-diamond bonding.

As merely one example, ASTM B886-03 (2008) provides a suitable standard for measuring the specific magnetic saturation and ASTM B887-03 (2008) e1 provides a suitable standard for measuring the coercivity of the PCD. Although both ASTM B886-03 (2008) and ASTM B887-03 (2008) e1 are directed to standards for measuring magnetic properties of cemented carbide materials, either standard may be used to determine the magnetic properties of PCD. A KOERZIMAT CS 1.096 instrument (commercially available from Foerster Instruments of Pittsburgh, Pa.) is one suitable instrument that may be used to measure the specific magnetic saturation and the coercivity of the PCD.

Generally, as the sintering pressure that is used to form the PCD increases, the coercivity may increase and the magnetic saturation may decrease. The PCD defined collectively by the bonded diamond grains and the metal-solvent catalyst may exhibit a coercivity of about 115 Oe or more and a metal-solvent catalyst content of less than about 7.5 wt % as indicated by a specific magnetic saturation of about 15 G·cm$^3$/g or less. In a more detailed embodiment, the coercivity of the PCD may be about 115 Oe to about 250 Oe and the specific magnetic saturation of the PCD may be greater than 0 G·cm$^3$/g to about 15 G·cm$^3$/g. In an even more detailed embodiment, the coercivity of the PCD may be about 115 Oe to about 175 Oe and the specific magnetic saturation of the PCD may be about 5 G·cm$^3$/g to about 15 G·cm$^3$/g. In yet an even more detailed embodiment, the coercivity of the PCD may be about 155 Oe to about 175 Oe and the specific magnetic saturation of the PCD may be about 10 G·cm$^3$/g to about 15 G·cm$^3$/g. The specific permeability (i.e., the ratio of specific magnetic saturation to coercivity) of the PCD may be about 0.10 or less, such as about 0.060 to about 0.090. Despite the average grain size of the bonded diamond grains being less than about 30 μm, the metal-solvent catalyst content in the PCD may be less than about 7.5 wt % resulting in a desirable thermal stability.

In one embodiment, diamond particles having an average particle size of about 18 μm to about 20 μm are positioned adjacent to a cobalt-cemented tungsten carbide substrate and subjected to an HPHT process at a temperature of about 1390° C. to about 1430° C. and a pressure of about 7.8 GPa to about 8.5 GPa. The PCD so-formed as a PCD table bonded to the substrate may exhibit a coercivity of about 155 Oe to about 175 Oe, a specific magnetic saturation of about 10 G·cm³/g to about 15 G·cm³/g, and a cobalt content of about 5 wt % to about 7.5 wt %.

In one or more embodiments, a specific magnetic saturation constant for the metal-solvent catalyst in the PCD may be about 185 G·cm³/g to about 215 G·cm³/g. For example, the specific magnetic saturation constant for the metal-solvent catalyst in the PCD may be about 195 G·cm³/g to about 205 G·cm³/g. It is noted that the specific magnetic saturation constant for the metal-solvent catalyst in the PCD may be composition dependent.

Generally, as the sintering pressure is increased above 7.5 GPa, a wear resistance of the PCD so-formed may increase. For example, the $G_{ratio}$ may be at least about $4.0 \times 10^6$, such as about $5.0 \times 10^6$ to about $15.0 \times 10^6$ or, more particularly, about $8.0 \times 10^6$ to about $15.0 \times 10^6$. In some embodiments, the $G_{ratio}$ may be at least about $30.0 \times 10^6$. The $G_{ratio}$, is the ratio of the volume of workpiece cut to the volume of PCD worn away during the cutting process. An example of suitable parameters that may be used to determine a $G_{ratio}$ of the PCD are a depth of cut for the PCD cutting element of about 0.254 mm, a back rake angle for the PCD cutting element of about 20 degrees, an in-feed for the PCD cutting element of about 6.35 mm/rev, a rotary speed of the workpiece to be cut of about 101 rpm, and the workpiece may be made from Barre granite having a 914 mm outer diameter and a 254 mm inner diameter. During the $G_{ratio}$ test, the workpiece is cooled with a coolant, such as water.

In addition to the aforementioned $G_{ratio}$, despite the presence of the metal-solvent catalyst in the PCD, the PCD may exhibit a thermal stability that is close to, substantially the same as, or greater than a partially leached PCD material formed by sintering a substantially similar diamond particle formulation at a lower sintering pressure (e.g., up to about 5.5 GPa) and in which the metal-solvent catalyst (e.g., cobalt) is leached therefrom to a depth of about 60 μm to about 100 μm from a working surface. The thermal stability of the PCD may be evaluated by measuring the distance cut in a workpiece prior to catastrophic failure, without using coolant, in a vertical lathe test (e.g., vertical turret lathe or a vertical boring mill). An example of suitable parameters that may be used to determine thermal stability of the PCD are a depth of cut for the PCD cutting element of about 1.27 mm, a back rake angle for the PCD cutting element of about 20 degrees, an in-feed for the PCD cutting element of about 1.524 mm/rev, a cutting speed of the workpiece to be cut of about 1.78 msec, and the workpiece may be made from Barre granite having a 914 mm outer diameter and a 254 mm inner diameter. In an embodiment, the distance cut in a workpiece prior to catastrophic failure as measured in the above-described vertical lathe test may be at least about 1300 m, such as about 1300 m to about 3950 m.

PCD formed by sintering diamond particles having the same diamond particle size distribution as a PCD embodiment of the invention, but sintered at a pressure of, for example, up to about 5.5 GPa and at temperatures in which diamond is stable may exhibit a coercivity of about 100 Oe or less and/or a specific magnetic saturation of about 16 G·cm³/g or more. Thus, in one or more embodiments of the invention, PCD exhibits a metal-solvent catalyst content of less than 7.5 wt % and a greater amount of diamond-to-diamond bonding between diamond grains than that of a PCD sintered at a lower pressure, but with the same precursor diamond particle size distribution and catalyst.

It is currently believed by the inventors that forming the PCD by sintering diamond particles at a pressure of at least about 7.5 GPa may promote nucleation and growth of diamond between the diamond particles being sintered so that the volume of the interstitial regions of the PCD so-formed is decreased compared to the volume of interstitial regions if the same diamond particle distribution was sintered at a pressure of, for example, up to about 5.5 GPa and at temperatures where diamond is stable. For example, the diamond may nucleate and grow from carbon provided by dissolved carbon in metal-solvent catalyst (e.g., liquefied cobalt) infiltrating into the diamond particles being sintered, partially graphitized diamond particles, carbon from a substrate, carbon from another source (e.g., graphite particles and/or fullerenes mixed with the diamond particles), or combinations of the foregoing. This nucleation and growth of diamond in combination with the sintering pressure of at least about 7.5 GPa may contribute to PCD so-formed having a metal-solvent catalyst content of less than about 7.5 wt %.

Figure 1B:
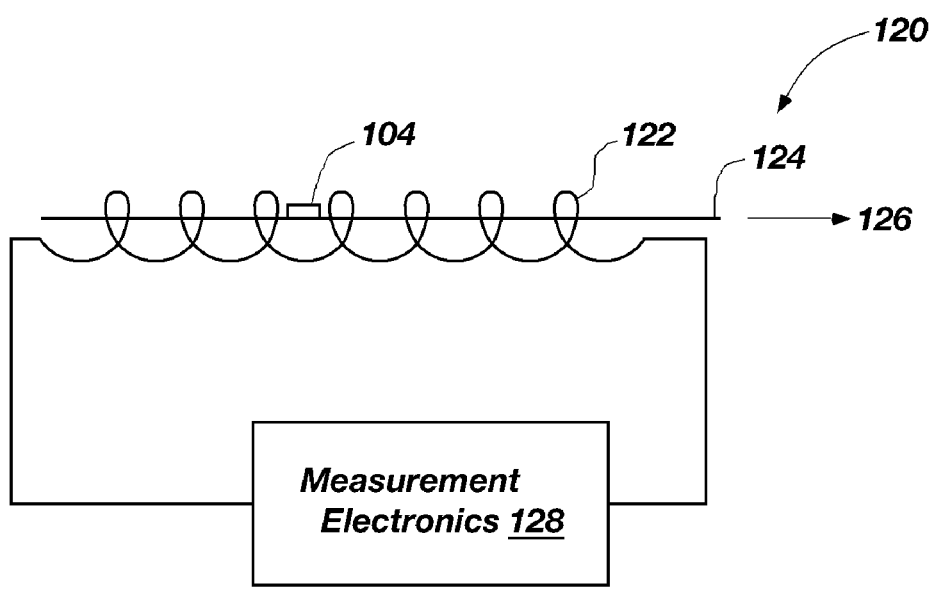
FIG. 1B is a schematic diagram of an example of a magnetic saturation measurement apparatus configured to measure a saturation magnetization of a PCD sample.
Figure 2:
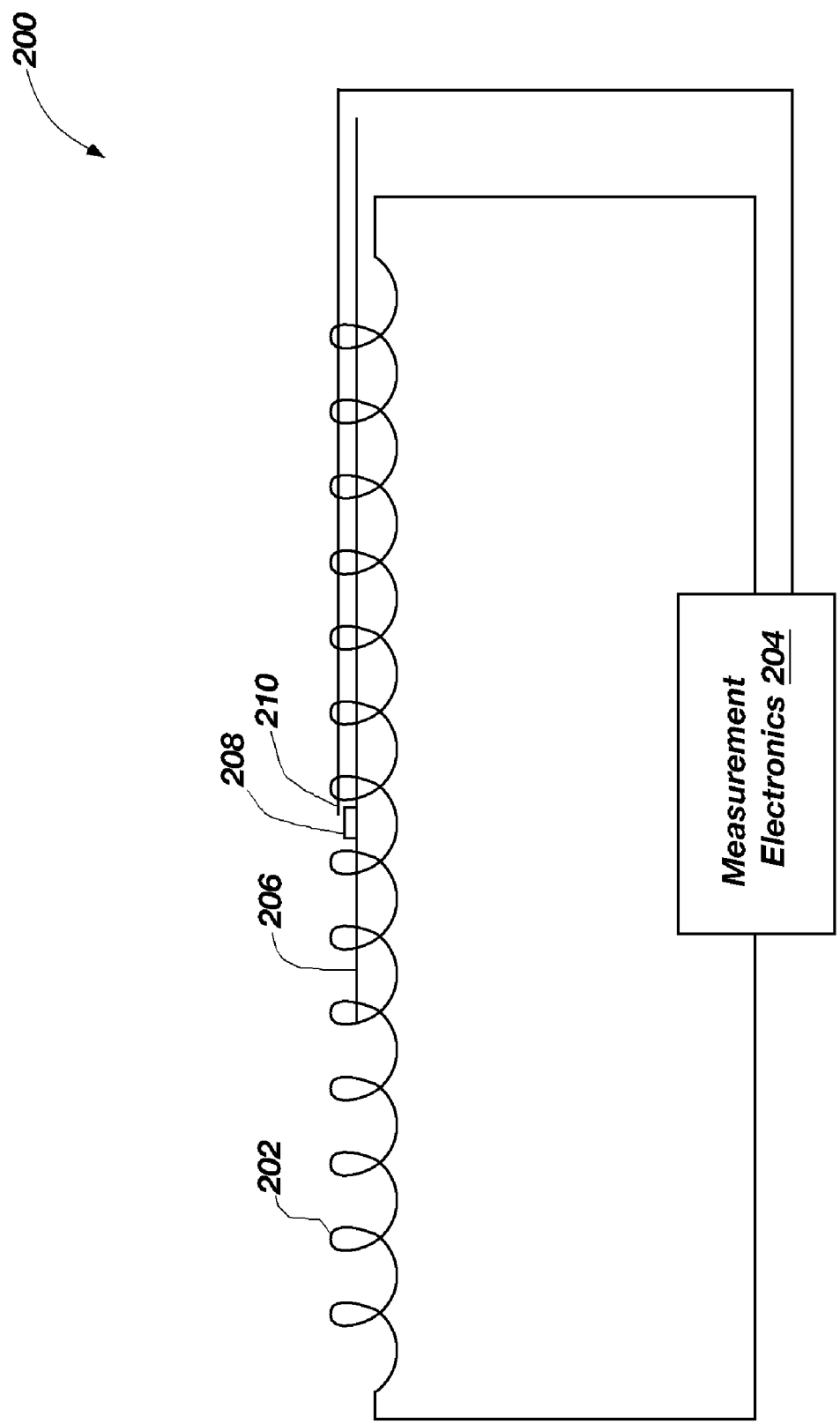
FIG. 2 is a schematic diagram of an example of a coercivity measurement apparatus configured to determine a coercivity of a PCD sample.

FIGS. 1A, 1B, and 2 schematically illustrate the manner in which the specific magnetic saturation and the coercivity of the PCD may be determined using an apparatus, such as the KOERZIMAT CS 1.096 instrument. FIG. 1A is a schematic diagram of an example of a magnetic saturation apparatus 100 configured to magnetize a PCD sample to saturation. The magnetic saturation apparatus 100 includes a saturation magnet 102 of sufficient strength to magnetize a PCD sample 104 to saturation. The saturation magnet 102 may be a permanent magnet or an electromagnet. In the illustrated embodiment, the saturation magnet 102 is a permanent magnet that defines an air gap 106, and the PCD sample 104 may be positioned on a sample holder 108 within the air gap 106. When the PCD sample 104 is light-weight, it may be secured to the sample holder 108 using, for example, double-sided tape or other adhesive so that the PCD sample 104 does not move responsive to the magnetic field from the saturation magnet 102 and the PCD sample 104 is magnetized approximately to saturation.

Referring to the schematic diagram of FIG. 1B, after magnetizing the PCD sample 104 approximately to saturation using the magnetic saturation apparatus 100, a magnetic saturation of the PCD sample 104 may be measured using a magnetic saturation measurement apparatus 120. The magnetic saturation measurement apparatus 120 includes a Helmholtz measuring coil 122 defining a passageway dimensioned so that the magnetized PCD sample 104 may be positioned therein on a sample holder 124. Once positioned in the passageway, the sample holder 124 supporting the magnetized PCD sample 104 may be moved axially along an axis direction 126 to induce a current in the Helmholtz measuring coil 122. Measurement electronics 128 are coupled to the Helmholtz measuring coil 122 and configured to calculate the magnetic saturation based upon the measured current passing through the Helmholtz measuring coil 122. The measurement electronics 128 may also be configured to calculate a weight percentage of magnetic material in the PCD sample 104 when the composition and magnetic characteristics of the metal-solvent catalyst in the PCD sample 104 are known, such as with iron, nickel, cobalt, and alloys thereof. Specific magnetic saturation may be calculated based upon the calculated magnetic saturation and the measured weight of the PCD sample 104.

The amount of metal-solvent catalyst in the PCD sample 104 may be determined using a number of different analytical techniques. For example, energy dispersive spectroscopy (e.g., EDAX), wavelength dispersive x-ray spectroscopy (e.g., WDX), and/or Rutherford backscattering spectroscopy may be employed to determine the amount of metal-solvent catalyst in the PCD sample 104.

If desired, a specific magnetic saturation constant of the metal-solvent catalyst content in the PCD sample 104 may be determined using an iterative approach. A value for the specific magnetic saturation constant of the metal-solvent catalyst in the PCD sample 104 may be iteratively chosen until a metal-solvent catalyst content calculated by the analysis software of the KOERZIMAT CS 1.096 instrument using the chosen value substantially matches the metal-solvent catalyst content determined via an analytical technique, such as energy dispersive spectroscopy, wavelength dispersive x-ray spectroscopy, and/or Rutherford backscattering spectroscopy.

FIG. 2 is a schematic diagram of a coercivity measurement apparatus 200 configured to determine a coercivity of a PCD sample. The coercivity measurement apparatus 200 includes a coil 202 and measurement electronics 204 coupled to the coil 202. The measurement electronics 204 are configured to pass a current through the coil 202 so that a magnetic field is generated. A sample holder 206 having a PCD sample 208 thereon may be positioned within the coil 202. A magnetization sensor 210 configured to measure a magnetization of the PCD sample 208 may be coupled to the measurement electronics 204 and positioned in proximity to the PCD sample 208.

During testing, the magnetic field generated by the coil 202 magnetizes the PCD sample 208 approximately to saturation. Then, the measurement electronics 204 apply a current so that the magnetic field generated by the coil 202 is increasingly reversed. The magnetization sensor 210 measures a magnetization of the PCD sample 208 resulting from application of the reversed magnetic field to the PCD sample 208. The measurement electronics 204 determine the coercivity of the PCD sample 208, which is a measurement of the reverse magnetic field at which the magnetization of the PCD sample 208 is zero.

Embodiments of Methods for Fabricating PCD

The PCD may be formed by sintering a mass of a plurality of diamond particles in the presence of a metal-solvent catalyst. The diamond particles may exhibit an average particle size of about 50 μm or less, such as about 30 μm or less, about 20 μm or less, about 10 μm to about 18 μm, or about 15 μm to about 18 μm. In some embodiments, the average particle size of the diamond particles may be about 10 μm or less, such as about 2 μm to about 5 μm or submicron.

In an embodiment, the diamond particles of the mass of diamond particles may comprise a relatively larger size and at least one relatively smaller size. As used herein, the phrases "relatively larger" and "relatively smaller" refer to particle sizes (by any suitable method) that differ by at least a factor of two (e.g., 30 μm and 15 μm). According to various embodiments, the mass of diamond particles may include a portion exhibiting a relatively larger size (e.g., 30 μm, 20 μm, 15 μm, 12 μm, 10 μm, 8 μm) and another portion exhibiting at least one relatively smaller size (e.g., 6 μm, 5 μm, 4 μm, 3 μm, 2 μm, 1 μm, 0.5 μm, less than 0.5 μm, 0.1 μm, less than 0.1 μm). In one embodiment, the mass of diamond particles may include a portion exhibiting a relatively larger size between about 10 μm and about 40 μm and another portion exhibiting a relatively smaller size between about 1 μm and 4 μm. In some embodiments, the mass of diamond particles may comprise three or more different sizes (e.g., one relatively larger size and two or more relatively smaller sizes), without limitation.

It is noted that the as-sintered diamond grain size may differ from the average particle size of the mass of diamond particles prior to sintering due to a variety of different physical processes, such as grain growth, diamond particles fracturing, carbon provided from another carbon source (e.g., dissolved carbon in the metal-solvent catalyst), or combinations of the foregoing. The metal-solvent catalyst (e.g., iron, nickel, cobalt, or alloys thereof) may be provided in particulate form mixed with the diamond particles, as a thin foil or plate placed adjacent to the mass of diamond particles, from a cemented carbide substrate including a metal-solvent catalyst, or combinations of the foregoing.

In order to efficiently sinter the mass of diamond particles, the mass may be enclosed in a pressure transmitting medium, such as a refractory metal can, graphite structure, pyrophyllite, and/or other suitable pressure transmitting structure to form a cell assembly. Examples of suitable gasket materials and cell structures for use in manufacturing PCD are disclosed in U.S. Pat. No. 6,338,754 and U.S. patent application Ser. No. 11/545,929, each of which is incorporated herein, in its entirety, by this reference. Another example of a suitable pressure transmitting material is pyrophyllite, which is commercially available from Wonderstone Ltd. of South Africa. The cell assembly, including the pressure transmitting medium and mass of diamond particles therein, is subjected to an HPHT process using an ultra-high pressure press at a temperature of at least about 1000° C. (e.g., about 1100° C. to about 2200° C., or about 1200° C. to about 1450° C.) and a pressure in the pressure transmitting medium of at least about 7.5 GPa (e.g., about 7.5 GPa to about 15 GPa) for a time sufficient to sinter the diamond particles together in the presence of the metal-solvent catalyst and form the PCD comprising bonded diamond grains defining interstitial regions occupied by the metal-solvent catalyst. For example, the pressure in the pressure transmitting medium employed in the HPHT process may be at least about 8.0 GPa, at least about 9.0 GPa, at least about 10.0 GPa, at least about 11.0 GPa, at least about 12.0 GPa, or at least about 14 GPa.

The pressure values employed in the HPHT processes disclosed herein refer to the pressure in the pressure transmitting medium at room temperature (e.g., about 25° C.) with application of pressure using an ultra-high pressure press and not the pressure applied to exterior of the cell assembly. The actual pressure in the pressure transmitting medium at sintering temperature may be slightly higher. The ultra-high pressure press may be calibrated at room temperature by embedding at least one calibration material that changes structure at a known pressure, such as PbTe, thallium, barium, or bismuth in the pressure transmitting medium. Further, optionally, a change in resistance may be measured across the at least one calibration material due to a phase change thereof. For example, PbTe exhibits a phase change at room temperature at about 6.0 GPa and bismuth exhibits a phase change at room temperature at about 7.7 GPa. Examples of suitable pressure calibration techniques are disclosed in G. Rousse, S. Klotz, A. M. Saitta, J. Rodriguez-Carvajal, M. I. McMahon, B. Couzinet, and M. Mezouar, "Structure of the Intermediate Phase of PbTe at High Pressure," Physical Review B: Condensed Matter and Materials Physics, 71, 224116 (2005) and D. L.

Decker, W. A. Bassett, L. Merrill, H. T. Hall, and J. D. Barnett, "High-Pressure Calibration: A Critical Review," J. Phys. Chem. Ref. Data, 1, 3 (1972).

In an embodiment, a pressure of at least about 7.5 GPa in the pressure transmitting medium may be generated by applying pressure to a cubic high-pressure cell assembly that encloses the mass of diamond particles to be sintered using anvils, with each anvil applying pressure to a different face of the cubic high-pressure assembly. In such an embodiment, a surface area of each anvil face of the anvils may be selectively dimensioned to facilitate application of pressure of at least about 7.5 GPa to the mass of diamond particles being sintered. For example, the surface area of each anvil may be less than about 12.0 cm$^2$, such as about 8 cm$^2$ to about 10 cm$^2$. The anvils may be made from a cobalt-cemented tungsten carbide or other material having a sufficient compressive strength to help reduce damage thereto through repetitive use in a high-volume commercial manufacturing environment. Optionally, as an alternative to or in addition to selectively dimensioning the surface area of each anvil face, two or more internal anvils may be embedded in the cubic high-pressure cell assembly to further intensify pressure. For example, the article W. Utsumi, N. Toyama, S. Endo and F. E. Fujita, "X-ray diffraction under ultrahigh pressure generated with sintered diamond anvils," J. Appl. Phys., 60, 2201 (1986) is incorporated herein, in its entirety, by this reference and discloses that sintered diamond anvils may be embedded in a cubic pressure transmitting medium for intensifying the pressure applied by an ultra-high pressure press to a workpiece also embedded in the cubic pressure transmitting medium.

PDC Embodiments and Methods of Fabricating PDCs

Figure 3A:
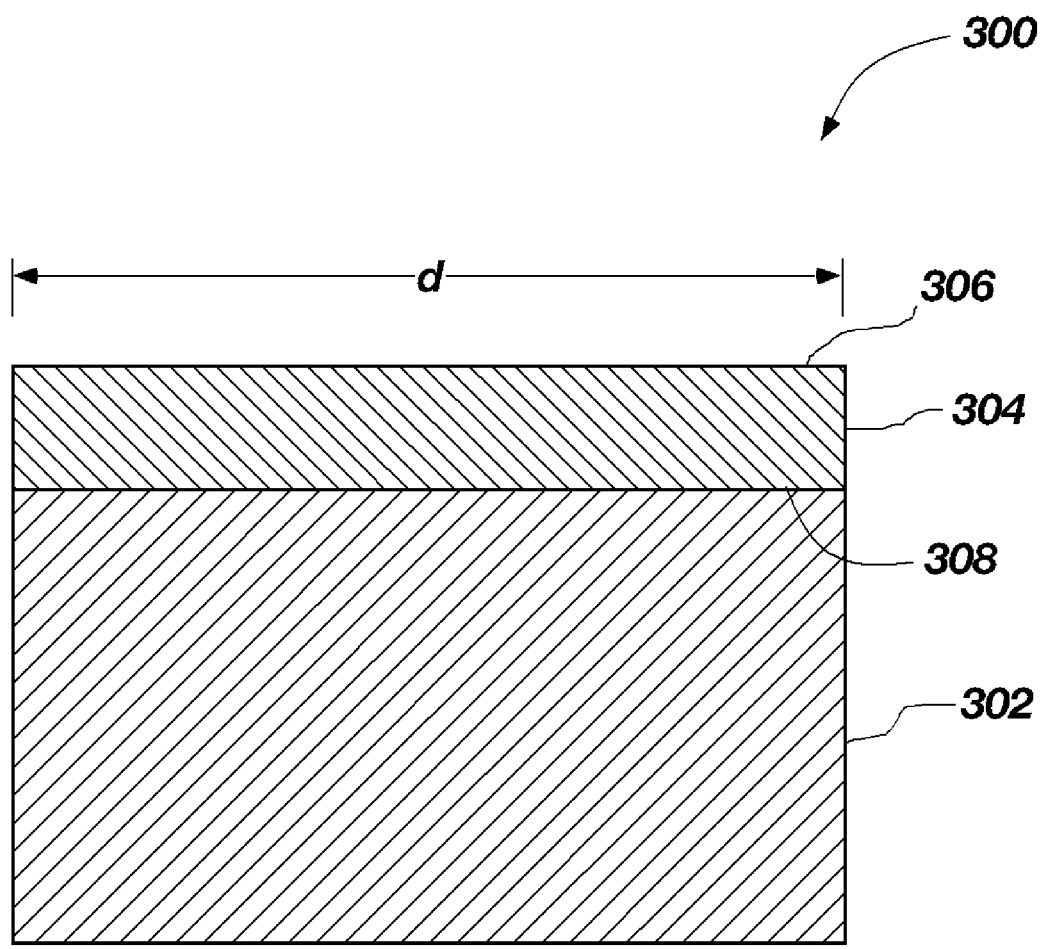
FIG. 3A is a cross-sectional view of an embodiment of a PDC including a PCD table formed from any of the PCD embodiments disclosed herein.

Referring to FIG. 3A, the PCD embodiments may be employed in a PDC for cutting applications, bearing applications, or many other applications. FIG. 3A is a cross-sectional view of an embodiment of a PDC 300. The PDC 300 includes a substrate 302 bonded to a PCD table 304. The PCD table 304 may be formed of PCD in accordance with any of the PCD embodiments disclosed herein. The PCD table 304 exhibits at least one working surface 306 and at least one lateral dimension "d" (e.g., a diameter). Although FIG. 1 shows the working surface 306 as substantially planar, the working surface 306 may be concave, convex, or another nonplanar geometry. The substrate 302 may be generally cylindrical or another selected configuration, without limitation. Although FIG. 1 shows an interfacial surface 308 of the substrate 302 as being substantially planar, the interfacial surface 308 may exhibit a selected nonplanar topography, such as a grooved, ridged, or other nonplanar interfacial surface. The substrate 302 may include, without limitation, cemented carbides, such as tungsten carbide, titanium carbide, chromium carbide, niobium carbide, tantalum carbide, vanadium carbide, or combinations thereof cemented with iron, nickel, cobalt, or alloys thereof. For example, in one embodiment, the substrate 302 comprises cobalt-cemented tungsten carbide.

Figure 4:
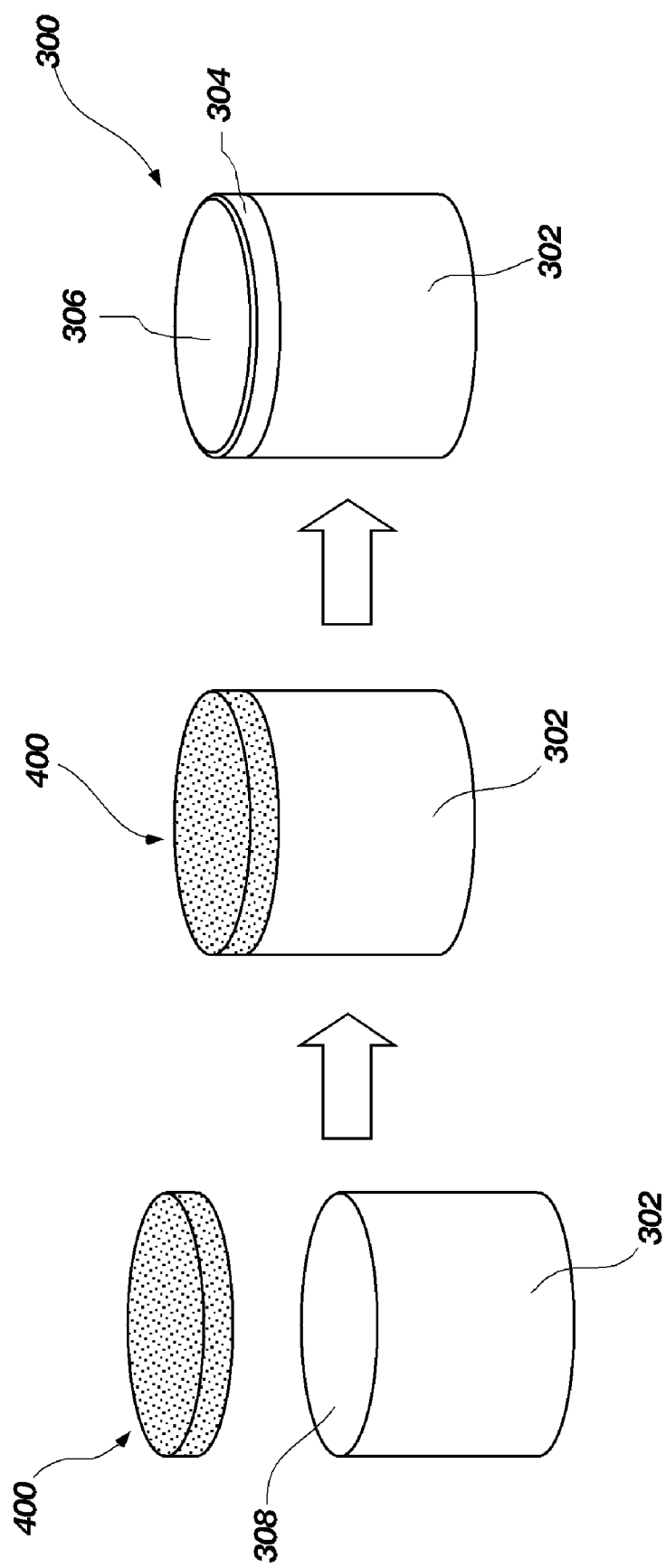
FIG. 4 is a schematic illustration of a method of fabricating the PDC shown in FIG. 3A.

FIG. 4 is a schematic illustration of an embodiment of a method for fabricating the PDC 300 shown in FIG. 3A. Referring to FIG. 4, a mass of diamond particles 400 having any of the above-mentioned average particle sizes and distributions (e.g., an average particle size of about 50 µm or less) is positioned adjacent to the interfacial surface 308 of the substrate 302. As previously discussed, the substrate 302 may include a metal-solvent catalyst. The mass of diamond particles 400 and substrate 302 may be subjected to an HPHT process using conditions previously described with respect to sintering the PCD embodiments disclosed herein. The PDC 300 so-formed includes the PCD table 304 that comprises PCD, formed of any of the PCD embodiments disclosed herein, integrally formed with the substrate 302 and bonded to the interfacial surface 308 of the substrate 302. If the substrate 302 includes a metal-solvent catalyst, the metal-solvent catalyst may liquefy and infiltrate the mass of diamond particles 400 to promote growth between adjacent diamond particles of the mass of diamond particles 400 to form the PCD table 304 comprised of a body of bonded diamond grains having the infiltrated metal-solvent catalyst interstitially disposed between bonded diamond grains. For example, if the substrate 302 is a cobalt-cemented tungsten carbide substrate, cobalt from the substrate 302 may be liquefied and infiltrate the mass of diamond particles 400 to catalyze formation of the PCD table 304.

Employing selectively dimensioned anvil faces and/or internal anvils in the ultra-high pressure press used to process the mass of diamond particles 400 and substrate 302 enables forming the at least one lateral dimension "d" of the PCD table 304 to be about 0.80 cm or more. Referring again to FIG. 3A, for example, the at least one lateral dimension "d" may be about 0.80 cm to about 3.0 cm and, in some embodiments, about 1.3 cm to about 1.9 cm or about 1.6 cm to about 1.9 cm. A representative volume of the PCD table 304 (or any PCD article of manufacture disclosed herein) formed using the selectively dimensioned anvil faces and/or internal anvils may be at least about 0.050 cm$^3$. For example, the volume may be about 0.25 cm$^3$ to at least about 1.25 cm$^3$ or about 0.1 cm$^3$ to at least about 0.70 cm$^3$. A representative volume for the PDC 300 may be about 0.4 cm$^3$ to at least about 4.6 cm$^3$, such as about 1.1 cm$^3$ to at least about 2.3 cm$^3$.

In other embodiments, a PCD table according to an embodiment may be separately formed using an HPHT sintering process and, subsequently, bonded to the interfacial surface 308 of the substrate 302 by brazing, using a separate HPHT bonding process, or any other suitable joining technique, without limitation. In yet another embodiment, a substrate may be formed by depositing a binderless carbide (e.g., tungsten carbide) via chemical vapor deposition onto the separately formed PCD table.

In any of the embodiments disclosed herein, substantially all or a selected portion of the metal-solvent catalyst may be removed (e.g., via leaching) from the PCD table. In an embodiment, metal-solvent catalyst in the PCD table may be removed to a selected depth from at least one exterior working surface (e.g., the working surface 306 and/or a sidewall working surface of the PCD table 304) so that only a portion of the interstitial regions are occupied by metal-solvent catalyst. For example, substantially all or a selected portion of the metal-solvent catalyst may be removed from the PCD table 304 so-formed in the PDC 300 to a selected depth from the working surface 306.

In another embodiment, a PCD table may be fabricated according to any of the disclosed embodiments in a first HPHT process, leached to remove substantially all of the metal-solvent catalyst from the interstitial regions between the bonded diamond grains, and subsequently bonded to a substrate in a second HPHT process. In the second HPHT process, an infiltrant from, for example, a cemented carbide substrate may infiltrate into the interstitial regions from which the metal-solvent catalyst was depleted. For example, the infiltrant may be cobalt that is swept-in from a cobalt-cemented tungsten carbide substrate. In one embodiment, the first and/or second HPHT process may be performed at a pressure of at least about 7.5 GPa. In one embodiment, the infiltrant may be leached from the infiltrated PCD table using a second acid leaching process following the second HPHT process.

In some embodiments, the pressure employed in the HPHT process used to fabricate the PDC 300 may be sufficient to reduce residual stresses in the PCD table 304 that develop during the HPHT process due to the thermal expansion mismatch between the substrate 302 and the PCD table 304. In such an embodiment, the principal stress measured on the working surface 306 of the PDC 300 may exhibit a value of about −345 MPa to about 0 MPa, such as about −289 MPa. For example, the principal stress measured on the working surface 306 may exhibit a value of about −345 MPa to about 0 MPa. A conventional PDC fabricated using an HPHT process at a pressure below about 7.5 GPa may result in a PCD table thereof exhibiting a principal stress on a working surface thereof of about −1724 MPa to about −414 MPa, such as about −770 MPa.

Residual stress may be measured on the working surface 306 of the PCD table 304 of the PDC 300 as described in T. P. Lin, M. Hood, G. A. Cooper, and R. H. Smith, "Residual stresses in polycrystalline diamond compacts," J. Am. Ceram. Soc. 77, 6, 1562-1568 (1994). More particularly, residual strain may be measured with a rosette strain gage bonded to the working surface 306. Such strain may be measured for different levels of removal of the substrate 302 (e.g., as material is removed from the back of the substrate 302). Residual stress may be calculated from the measured residual strain data.

Figure 3B:
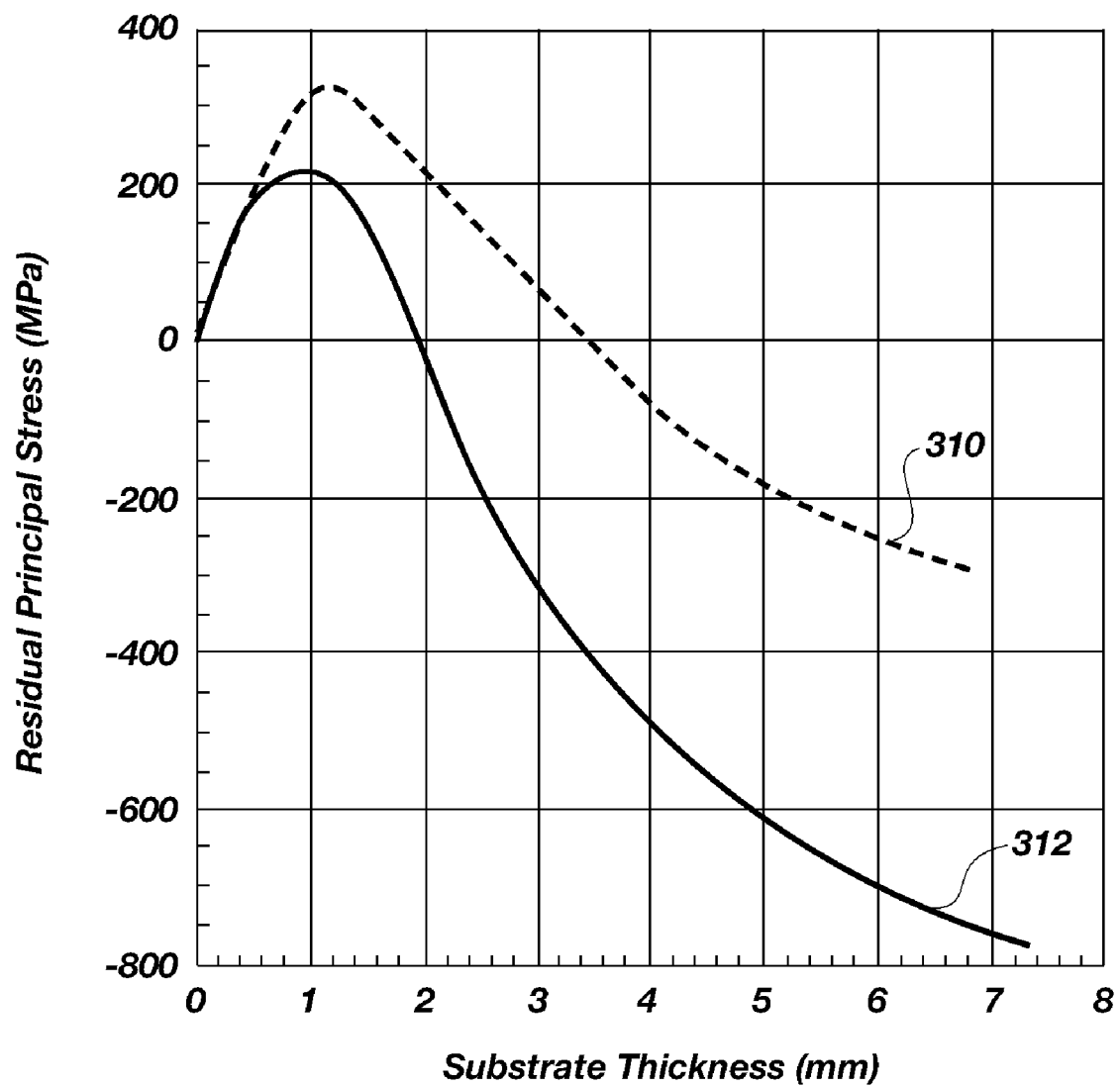
FIG. 3B is a graph illustrating residual principal stress versus substrate thickness that was measured in a PCD table of a PDC fabricated at a pressure above about 7.5 GPa and a PCD table of a conventionally formed PDC.

FIG. 3B is a graph of residual principal stress versus substrate thickness that was measured in a PCD table of a PDC fabricated at pressure above about 7.5 GPa in accordance with an embodiment of the invention and a PCD table of a conventionally formed PDC. The residual principal stress was determined using the technique described in the article referenced above by Lin et al. Curve 310 shows the measured residual principal stress on a working surface of the PDC fabricated at a pressure above about 7.5 GPa. The PDC that was fabricated at a pressure above about 7.5 GPa had a thickness dimension of about 1 mm and the substrate had a thickness dimension of about 7 mm and a diameter of about 13 mm. Curve 312 shows the measured residual principal stress on a working surface of a PCD table of a conventionally PDC fabricated at pressure below about 7.5 GPa. The PDC that was fabricated at a pressure below about 7.5 GPa had a thickness dimension of about 1 mm and the substrate had a thickness dimension of about 7 mm and a diameter of about 13 mm. The highest absolute value of the residual principal stress occurs with the full substrate length of about 7 mm. As shown by the curves 310 and 312, increasing the pressure, employed in the HPHT process used to fabricate a PDC, above about 7.5 GPa may reduce the highest absolute value of the principal residual stress in a PCD table thereof by about 60% relative to a conventionally fabricated PDC. For example, at the full substrate length, the absolute value of the principal residual stress in the PCD table fabricated at a pressure above about 7.5 GPa is about 60% less than the absolute value of the principal residual stress in the PCD table of the conventionally fabricated PDC.

The following working examples provide further detail about the magnetic properties of PCD tables of PDCs fabricated in accordance with the principles of some of the specific embodiments of the invention. The magnetic properties of each PCD table listed in Tables I-IV were tested using a KOERZIMAT CS 1.096 instrument that is commercially available from Foerster Instruments of Pittsburgh, Pa. The specific magnetic saturation of each PCD table was measured in accordance with ASTM B886-03 (2008) and the coercivity of each PCD table was measured using ASTM B887-03 (2008)e1 using a KOERZIMAT CS 1.096 instrument. The amount of cobalt-based metal-solvent catalyst in the tested PCD tables was determined using energy dispersive spectroscopy and Rutherford backscattering spectroscopy. The specific magnetic saturation constant of the cobalt-based metal-solvent catalyst in the tested PCD tables was determined to be about 201 G·cm$^3$/g using an iterative analysis as previously described. When a value of 201 G·cm$^3$/g was used for the specific magnetic saturation constant of the cobalt-based metal-solvent catalyst, the calculated amount of the cobalt-based metal-solvent catalyst in the tested PCD tables using the analysis software of the KOERZIMAT CS 1.096 instrument substantially matched the measurements using energy dispersive spectroscopy and Rutherford spectroscopy.

Table I below lists PCD tables that were fabricated in accordance with the principles of certain embodiments of the invention discussed above. Each PCD table was fabricated by placing a mass of diamond particles having the listed average diamond particle size adjacent to a cobalt-cemented tungsten carbide substrate in a niobium container, placing the container in a high-pressure cell medium, and subjecting the high-pressure cell medium and the container therein to an HPHT process using an HPHT cubic press to form a PCD table bonded to the substrate. The surface area of each anvil of the HPHT press and the hydraulic line pressure used to drive the anvils were selected so that the sintering pressure was at least about 7.8 GPa. The temperature of the HPHT process was about 1400° C. and the sintering pressure was at least about 7.8 GPa. The sintering pressures listed in Table I refer to the pressure in the high-pressure cell medium at room temperature, and the actual sintering pressures at the sintering temperature are believed to be greater. After the HPHT process, the PCD table was removed from the substrate by grinding away the substrate. However, the substrate may also be removed using electro-discharge machining or another suitable method.

TABLE I

Selected Magnetic Properties of PCD Tables Fabricated According to Embodiments of the Invention

|   | Average Diamond Particle Size (μm) | Sintering Pressure (GPa) | Specific Magnetic Saturation (G·cm$^3$/g) | Calculated Co wt % | Coercivity (Oe) | Specific Permeability (G·cm$^3$/g·Oe) |
|---|---|---|---|---|---|---|
| 1 | 20 | 7.8 | 11.15 | 5.549 | 130.2 | 0.08564 |
| 2 | 19 | 7.8 | 11.64 | 5.792 | 170.0 | 0.06847 |
| 3 | 19 | 7.8 | 11.85 | 5.899 | 157.9 | 0.07505 |
| 4 | 19 | 7.8 | 11.15 | 5.550 | 170.9 | 0.06524 |
| 5 | 19 | 7.8 | 11.43 | 5.689 | 163.6 | 0.06987 |

TABLE I-continued

Selected Magnetic Properties of PCD Tables Fabricated According to Embodiments of the Invention

| | Average Diamond Particle Size (μm) | Sintering Pressure (GPa) | Specific Magnetic Saturation (G · cm³/g) | Calculated Co wt % | Coercivity (Oe) | Specific Permeability (G · cm³/g · Oe) |
|---|---|---|---|---|---|---|
| 6 | 19 | 7.8 | 10.67 | 5.150 | 146.9 | 0.07263 |
| 7 | 19 | 7.8 | 10.76 | 5.357 | 152.3 | 0.07065 |
| 8 | 19 | 7.8 | 10.22 | 5.087 | 145.2 | 0.07039 |
| 9 | 19 | 7.8 | 10.12 | 5.041 | 156.6 | 0.06462 |
| 10 | 19 | 7.8 | 10.72 | 5.549 | 137.1 | 0.07819 |
| 11 | 11 | 7.8 | 12.52 | 6.229 | 135.3 | 0.09254 |
| 12 | 11 | 7.8 | 12.78 | 6.362 | 130.5 | 0.09793 |
| 13 | 11 | 7.8 | 12.69 | 6.315 | 134.6 | 0.09428 |
| 14 | 11 | 7.8 | 13.20 | 6.569 | 131.6 | 0.1003 |

Table II below lists conventional PCD tables that were fabricated. Each PCD table listed in Table II was fabricated by placing a mass of diamond particles having the listed average diamond particle size adjacent to a cobalt-cemented tungsten carbide substrate in a niobium container, placing the container in a high-pressure cell medium, and subjecting the high-pressure cell medium and the container therein to an HPHT process using an HPHT cubic press to form a PCD table bonded to the substrate. The surface area of each anvil of the HPHT press and the hydraulic line pressure used to drive the anvils were selected so that the sintering pressure was about 4.6 GPa. Except for samples 15, 16, 18, and 19, which were subjected to a temperature of about 1430° C., the temperature of the HPHT process was about 1400° C. and the sintering pressure was about 4.6 GPa. The sintering pressures listed in Table II refer to the pressure in the high-pressure cell medium at room temperature. After the HPHT process, the PCD table was removed from the cobalt-cemented tungsten carbide substrate by grinding away the cobalt-cemented tungsten carbide substrate.

TABLE II

Selected Magnetic Properties of Several Conventional PCD Tables

| | Average Diamond Particle Size (μm) | Sintering Pressure (GPa) | Specific Magnetic Saturation (G · cm³/g) | Calculated Co wt % | Coercivity (Oe) | Specific Permeability (G · cm³/g · Oe) |
|---|---|---|---|---|---|---|
| 15 | 20 | 4.61 | 19.30 | 9.605 | 94.64 | 0.2039 |
| 16 | 20 | 4.61 | 19.52 | 9.712 | 96.75 | 0.2018 |
| 17 | 20 | 4.61 | 19.87 | 9.889 | 94.60 | 0.2100 |
| 18 | 20 | 5.08 | 18.61 | 9.260 | 94.94 | 0.1960 |
| 19 | 20 | 5.08 | 18.21 | 9.061 | 100.4 | 0.1814 |
| 20 | 20 | 5.86 | 16.97 | 8.452 | 108.3 | 0.1567 |
| 21 | 20 | 4.61 | 17.17 | 8.543 | 102.0 | 0.1683 |
| 22 | 20 | 4.61 | 17.57 | 8.745 | 104.9 | 0.1675 |
| 23 | 20 | 5.08 | 16.10 | 8.014 | 111.2 | 0.1448 |
| 24 | 20 | 5.08 | 16.79 | 8.357 | 107.1 | 0.1568 |

As shown in Tables I and II, the conventional PCD tables listed in Table II exhibit a higher cobalt content therein than the PCD tables listed in Table I as indicated by the relatively higher specific magnetic saturation values. Additionally, the conventional PCD tables listed in Table II exhibit a lower coercivity indicative of a relatively greater mean free path between diamond grains, and thus may indicate relatively less diamond-to-diamond bonding between the diamond grains. Thus, the PCD tables according to examples of the invention listed in Table I may exhibit significantly less cobalt therein and a lower mean free path between diamond grains than the PCD tables listed in Table II.

Table III below lists conventional PCD tables that were obtained from PDCs. Each PCD table listed in Table III was separated from a cobalt-cemented tungsten carbide substrate bonded thereto by grinding.

TABLE III

Selected Magnetic Properties of Several Conventional PCD Tables

| | Specific Magnetic Saturation (G · cm³/g) | Calculated Co wt % | Coercivity (Oe) | Specific Permeability (G · cm³/g · Oe) |
|---|---|---|---|---|
| 25 | 17.23 | 8.572 | 140.4 | 0.1227 |
| 26 | 16.06 | 7.991 | 150.2 | 0.1069 |
| 27 | 15.19 | 7.560 | 146.1 | 0.1040 |
| 28 | 17.30 | 8.610 | 143.2 | 0.1208 |
| 29 | 17.13 | 8.523 | 152.1 | 0.1126 |
| 30 | 17.00 | 8.458 | 142.5 | 0.1193 |
| 31 | 17.08 | 8.498 | 147.2 | 0.1160 |
| 32 | 16.10 | 8.011 | 144.1 | 0.1117 |

Table IV below lists conventional PCD tables that were obtained from PDCs. Each PCD table listed in Table IV was separated from a cobalt-cemented tungsten carbide substrate bonded thereto by grinding the substrate away. Each PCD table listed in Table IV and tested had a leached region from which cobalt was depleted and an unleached region in which cobalt is interstitially disposed between bonded diamond grains. The leached region was not removed. However, to determine the specific magnetic saturation and the coercivity of the unleached region of the PCD table having metal-solvent catalyst occupying interstitial regions therein, the leached region may be ground away so that only the unleached region of the PCD table remains. It is expected that the leached region causes the specific magnetic saturation to be lower and the coercivity to be higher than if the leached region was removed and the unleached region was tested.

TABLE IV

Selected Magnetic Properties of Several Conventional Leached PCD Tables

| | Specific Magnetic Saturation (G · cm³/g) | Calculated Co wt % | Coercivity (Oe) | Specific Permeability (G · cm³/g · Oe) |
|---|---|---|---|---|
| 33 | 17.12 | 8.471 | 143.8 | 0.1191 |
| 34 | 13.62 | 6.777 | 137.3 | 0.09920 |
| 35 | 15.87 | 7.897 | 140.1 | 0.1133 |
| 36 | 12.95 | 6.443 | 145.5 | 0.0890 |
| 37 | 13.89 | 6.914 | 142.0 | 0.09782 |
| 38 | 13.96 | 6.946 | 146.9 | 0.09503 |
| 39 | 13.67 | 6.863 | 133.8 | 0.1022 |
| 40 | 12.80 | 6.369 | 146.3 | 0.08749 |

As shown in Tables I, III, and IV, the conventional PCD tables of Tables III and IV exhibit a higher cobalt content therein than the PCD tables listed in Table I as indicated by the relatively higher specific magnetic saturation values. This is believed by the inventors to be a result of the PCD tables listed in Tables III and IV being formed by sintering diamond particles having a relatively greater percentage of fine diamond particles than the diamond particle formulations used to fabricate the PCD tables listed in Table I.

Embodiments of Applications for PCD and PDCs

Figure 8:
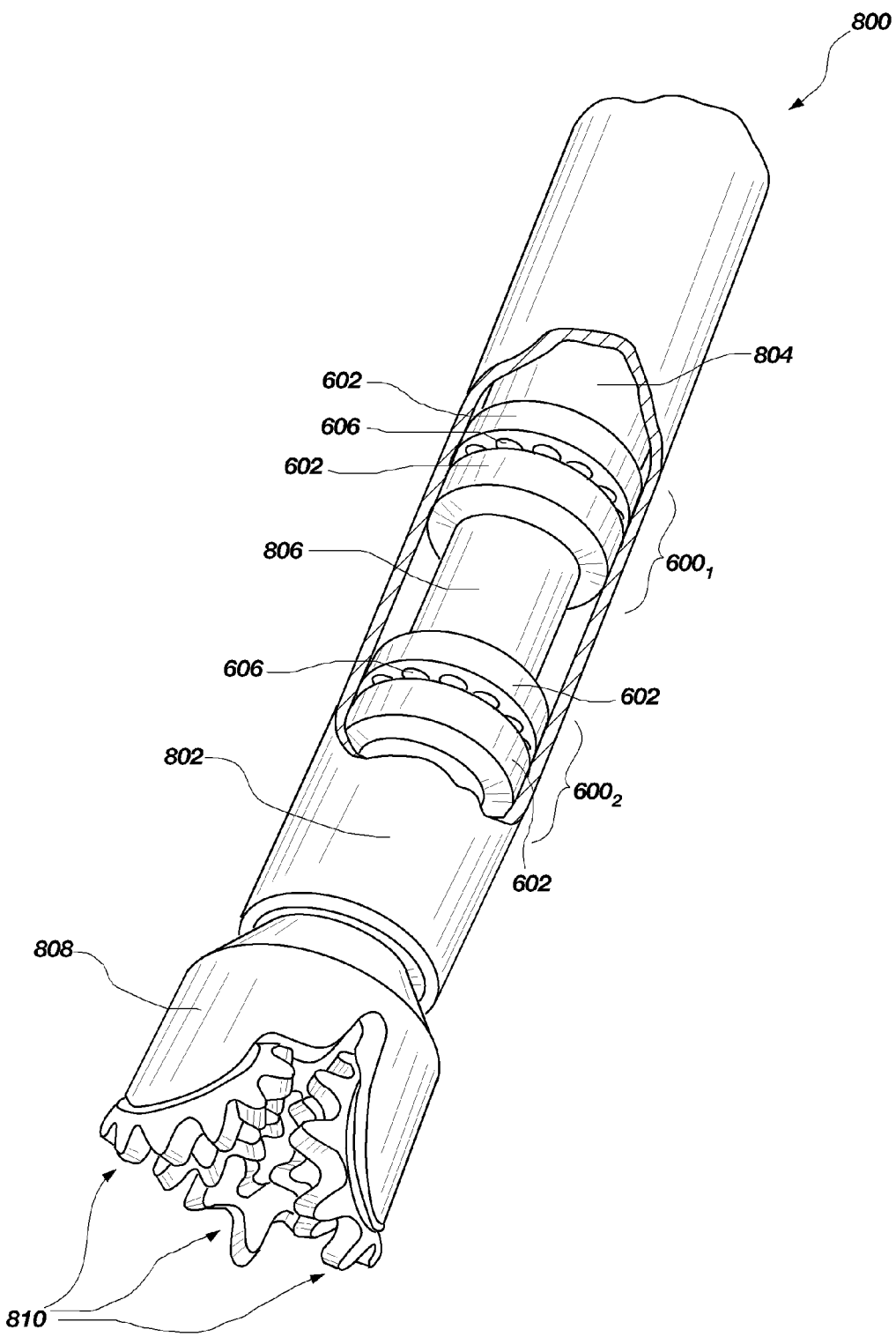
FIG. 8 is a schematic isometric cut-away view of an embodiment of a subterranean drilling system including the thrust-bearing apparatus shown in FIG. 6.
Figure 9:
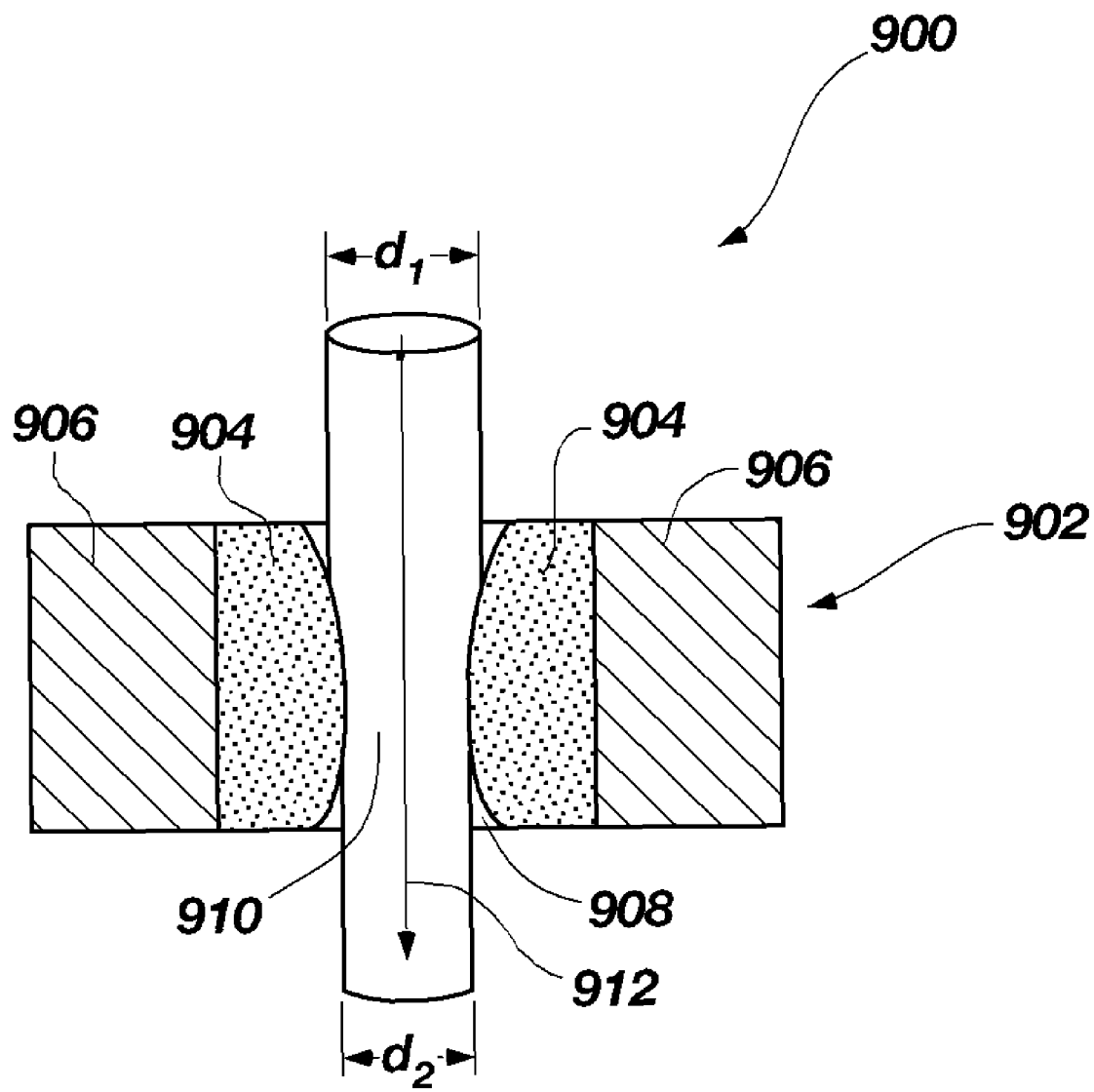
FIG. 9 is a side cross-sectional view of an embodiment of a wire-drawing die that employs a PDC fabricated in accordance with the principles described herein.

The disclosed PCD and PDC embodiments may be used in a number of different applications including, but not limited to, use in a rotary drill bit (FIGS. 5A and 5B), a thrust-bearing apparatus (FIG. 6), a radial bearing apparatus (FIG. 7), a subterranean drilling system (FIG. 8), and a wire-drawing die (FIG. 9). The various applications discussed above are merely some examples of applications in which the PCD and PDC embodiments may be used. Other applications are contemplated, such as employing the disclosed PCD and PDC embodiments in friction stir welding tools.

Figure 5A:
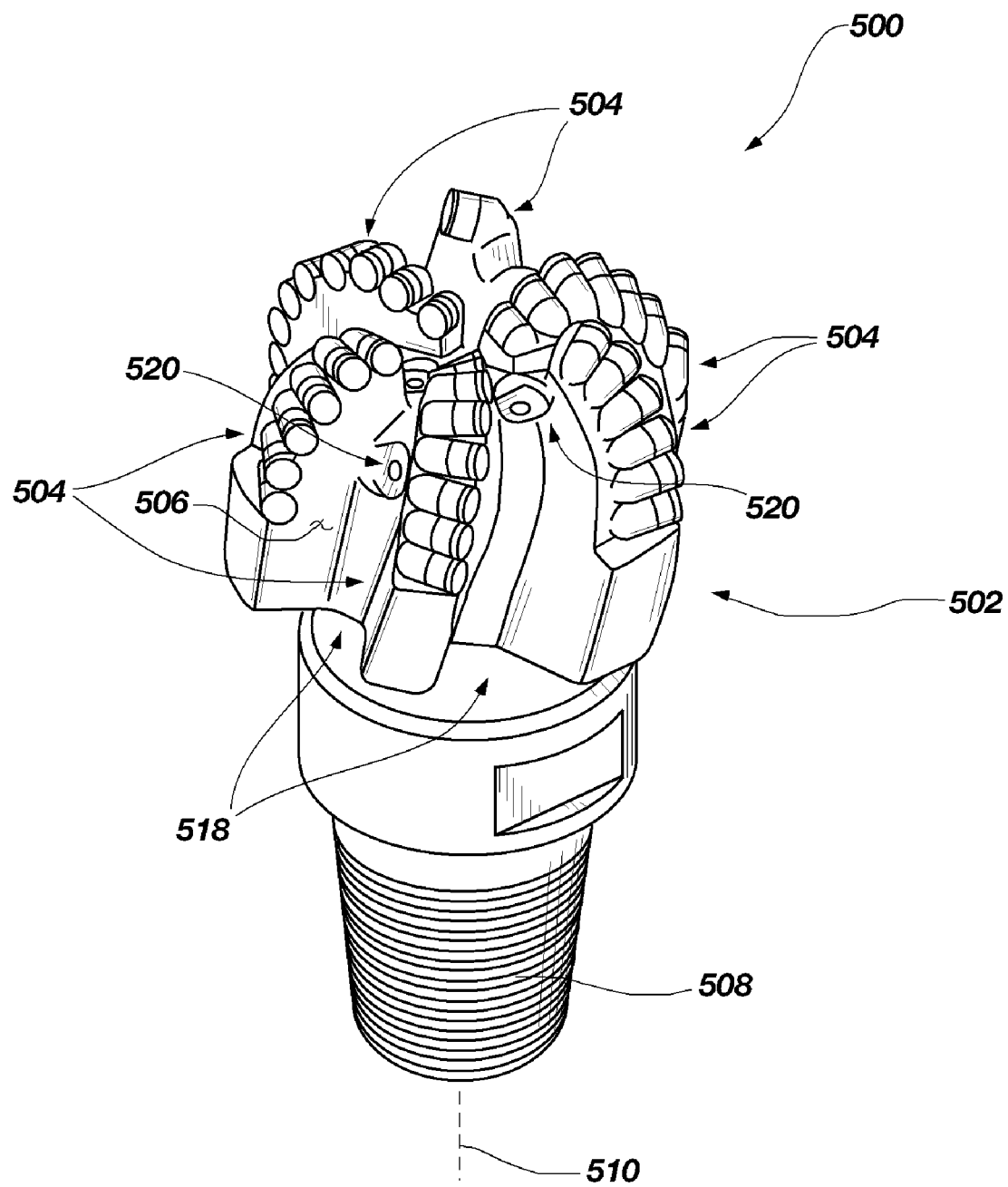
FIG. 5A is an isometric view of an embodiment of a rotary drill bit that may employ one or more of the disclosed PDC embodiments.
Figure 5B:
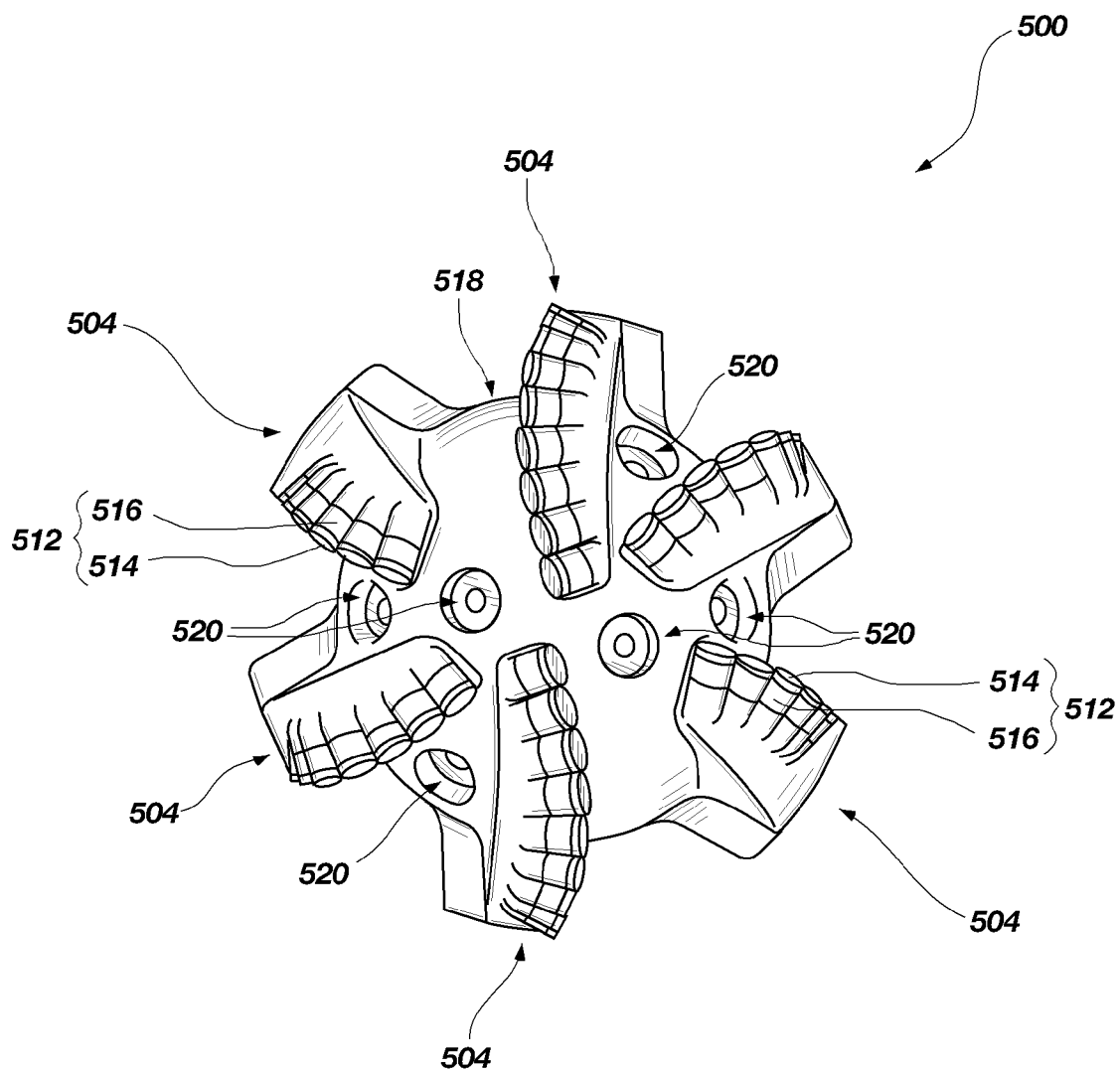
FIG. 5B is a top elevation view of the rotary drill bit shown in FIG. 5A.

FIG. 5A is an isometric view and FIG. 5B is a top elevation view of an embodiment of a rotary drill bit 500. The rotary drill bit 500 includes at least one PDC configured according to any of the previously described PDC embodiments. The rotary drill bit 500 comprises a bit body 502 that includes radially and longitudinally extending blades 504 with leading faces 506, and a threaded pin connection 508 for connecting the bit body 502 to a drilling string. The bit body 502 defines a leading end structure for drilling into a subterranean formation by rotation about a longitudinal axis 510 and application of weight-on-bit. At least one PDC cutting element, configured according to any of the previously described PDC embodiments (e.g., the PDC 300 shown in FIG. 3A), may be affixed to the bit body 502. With reference to FIG. 5B, a plurality of PDCs 512 are secured to the blades 504. For example, each PDC 512 may include a PCD table 514 bonded to a substrate 516. More generally, the PDCs 512 may comprise any PDC disclosed herein, without limitation. In addition, if desired, in some embodiments, a number of the PDCs 512 may be conventional in construction. Also, circumferentially adjacent blades 504 define so-called junk slots 518 therebetween, as known in the art. Additionally, the rotary drill bit 500 may include a plurality of nozzle cavities 520 for communicating drilling fluid from the interior of the rotary drill bit 500 to the PDCs 512.

FIGS. 5A and 5B merely depict an embodiment of a rotary drill bit that employs at least one cutting element comprising a PDC fabricated and structured in accordance with the disclosed embodiments, without limitation. The rotary drill bit 500 is used to represent any number of earth-boring tools or drilling tools, including, for example, core bits, roller-cone bits, fixed-cutter bits, eccentric bits, bicenter bits, reamers, reamer wings, or any other downhole tool including PDCs, without limitation.

The PCD and/or PDCs disclosed herein (e.g., the PDC 300 shown in FIG. 3A) may also be utilized in applications other than rotary drill bits. For example, the disclosed PDC embodiments may be used in thrust-bearing assemblies, radial bearing assemblies, wire-drawing dies, artificial joints, machining elements, and heat sinks.

Figure 6:
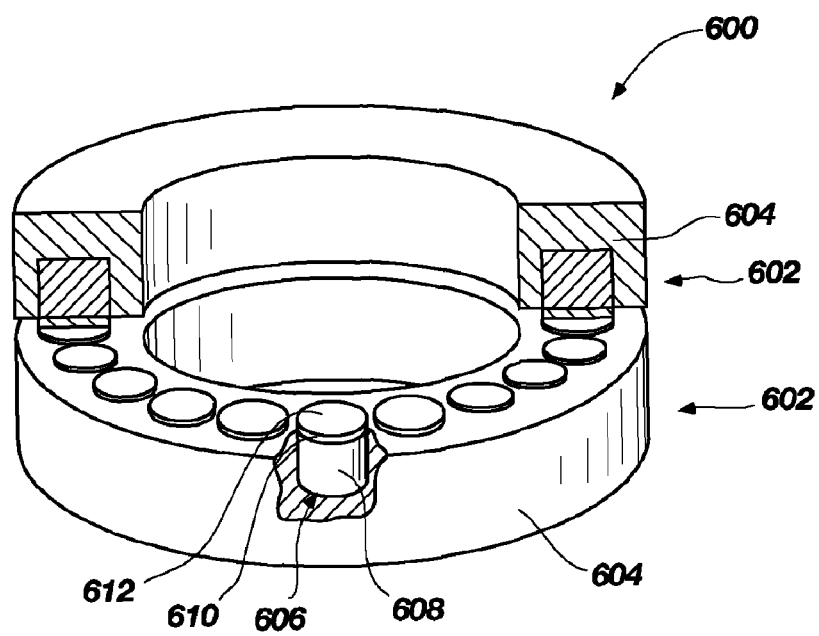
FIG. 6 is an isometric cut-away view of an embodiment of a thrust-bearing apparatus that may utilize one or more of the disclosed PDC embodiments.

FIG. 6 is an isometric cut-away view of an embodiment of a thrust-bearing apparatus 600, which may utilize any of the disclosed PDC embodiments as bearing elements. The thrust-bearing apparatus 600 includes respective thrust-bearing assemblies 602. Each thrust-bearing assembly 602 includes an annular support ring 604 that may be fabricated from a material, such as carbon steel, stainless steel, or another suitable material. Each support ring 604 includes a plurality of recesses (not labeled) that receive a corresponding bearing element 606. Each bearing element 606 may be mounted to a corresponding support ring 604 within a corresponding recess by brazing, press-fitting, using fasteners, or another suitable mounting technique. One or more, or all of bearing elements 606 may be configured according to any of the disclosed PDC embodiments. For example, each bearing element 606 may include a substrate 608 and a PCD table 610, with the PCD table 610 including a bearing surface 612.

In use, the bearing surfaces 612 of one of the thrust-bearing assemblies 602 bear against the opposing bearing surfaces 612 of the other one of the bearing assemblies 602. For example, one of the thrust-bearing assemblies 602 may be operably coupled to a shaft to rotate therewith and may be termed a "rotor." The other one of the thrust-bearing assemblies 602 may be held stationary and may be termed a "stator."

Figure 7:
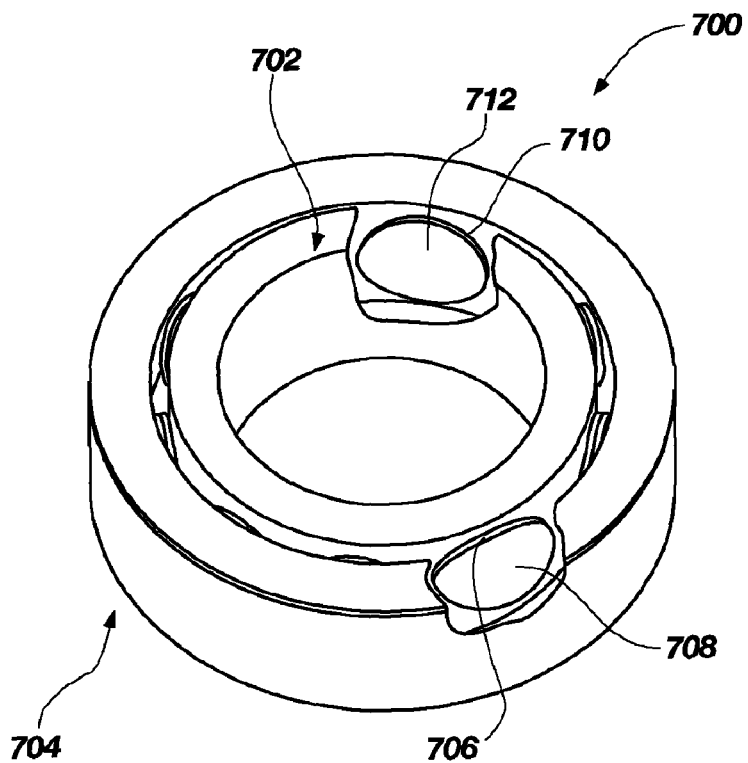
FIG. 7 is an isometric cut-away view of an embodiment of a radial bearing apparatus that may utilize one or more of the disclosed PDC embodiments.

FIG. 7 is an isometric cut-away view of an embodiment of a radial bearing apparatus 700, which may utilize any of the disclosed PDC embodiments as bearing elements. The radial bearing apparatus 700 includes an inner race 702 positioned generally within an outer race 704. The outer race 704 includes a plurality of bearing elements 706 affixed thereto that have respective bearing surfaces 708. The inner race 702 also includes a plurality of bearing elements 710 affixed thereto that have respective bearing surfaces 712. One or more, or all of the bearing elements 706 and 710 may be configured according to any of the PDC embodiments disclosed herein. The inner race 702 is positioned generally within the outer race 704, and thus the inner race 702 and outer race 704 may be configured so that the bearing surfaces 708 and 712 may at least partially contact one another and move relative to each other as the inner race 702 and outer race 704 rotate relative to each other during use.

The radial bearing apparatus 700 may be employed in a variety of mechanical applications. For example, so-called "roller-cone" rotary drill bits may benefit from a radial-bearing apparatus disclosed herein. More specifically, the inner race 702 may be mounted to a spindle of a roller cone and the outer race 704 may be mounted to an inner bore formed within a cone and such an outer race 704 and inner race 702 may be assembled to form a radial bearing apparatus.

Referring to FIG. 8, the thrust-bearing apparatus 600 and/or radial bearing apparatus 700 may be incorporated in a subterranean drilling system. FIG. 8 is a schematic isometric cut-away view of a subterranean drilling system 800 that includes at least one of the thrust-bearing apparatuses 600 shown in FIG. 6 according to another embodiment. The subterranean drilling system 800 includes a housing 802 enclosing a downhole drilling motor 804 (i.e., a motor, turbine, or any other device capable of rotating an output shaft) that is operably connected to an output shaft 806. A first thrust-bearing apparatus 600$_1$ (FIG. 6) is operably coupled to the downhole drilling motor 804. A second thrust-bearing apparatus 600$_2$ (FIG. 6) is operably coupled to the output shaft 806. A rotary drill bit 808 configured to engage a subterranean formation and drill a borehole is connected to the output shaft 806. The rotary drill bit 808 is shown as a roller-cone bit including a plurality of roller cones 810. However, other embodiments may utilize different types of rotary drill bits, such as a so-called "fixed-cutter" drill bit shown in FIGS. 5A and 5B. As the borehole is drilled, pipe sections may be connected to the subterranean drilling system 800 to form a drill string capable of progressively drilling the borehole to a greater depth within the earth.

A first one of the thrust-bearing assemblies 602 of the thrust-bearing apparatus 600$_1$ is configured as a stator that does not rotate and a second one of the thrust-bearing assemblies 602 of the thrust-bearing apparatus 600$_1$ is configured as a rotor that is attached to the output shaft 806 and rotates with the output shaft 806. The on-bottom thrust generated when the drill bit 808 engages the bottom of the borehole may be carried, at least in part, by the first thrust-bearing apparatus 600$_1$. A first one of the thrust-bearing assemblies 602 of the thrust-bearing apparatus 600$_2$ is configured as a stator that does not rotate and a second one of the thrust-bearing assemblies 602 of the thrust-bearing apparatus 600$_2$ is configured as a rotor that is attached to the output shaft 806 and rotates with the output shaft 806. Fluid flow through the power section of the downhole drilling motor 804 may cause what is commonly referred to as "off-bottom thrust," which may be carried, at least in part, by the second thrust-bearing apparatus 600$_2$.

In operation, drilling fluid may be circulated through the downhole drilling motor 804 to generate torque and effect rotation of the output shaft 806 and the rotary drill bit 808 attached thereto so that a borehole may be drilled. A portion of the drilling fluid may also be used to lubricate opposing bearing surfaces of the bearing elements 606 of the thrust-bearing assemblies 602.

FIG. 9 is a side cross-sectional view of an embodiment of a wire-drawing die 900 that employs a PDC 902 fabricated in accordance with the teachings described herein. The PDC 902 includes an inner, annular PCD region 904 comprising any of the PCD tables described herein that is bonded to an outer cylindrical substrate 906 that may be made from the same materials as the substrate 302 shown in FIG. 3A. The PCD region 904 also includes a die cavity 908 formed therethrough configured for receiving and shaping a wire being drawn. The wire-drawing die 900 may be encased in a housing (e.g., a stainless steel housing), which is not shown, to allow for handling.

In use, a wire 910 of a diameter "$d_1$" is drawn through die cavity 908 along a wire-drawing axis 912 to reduce the diameter of the wire 910 to a reduced diameter "$d_2$."

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall have the same meaning as the word "comprising" and variants thereof (e.g., "comprise" and "comprises").

The invention claimed is:

1. Polycrystalline diamond, comprising:
    a plurality of diamond grains defining a plurality of interstitial regions;
    a metal-solvent catalyst occupying a substantial number of the plurality of interstitial regions, the metal-solvent catalyst present in an amount of about 1 weight % to about 6 weight %;
    wherein the plurality of diamond grains and the metal-solvent catalyst collectively exhibit a coercivity of about 115 Oersteds ("Oe") or more;
    wherein the plurality of diamond grains and the metal-solvent catalyst collectively exhibit a specific magnetic saturation of about 15 Gauss·cm$^3$/grams ("G·cm$^3$/g") or less;
    wherein the plurality of diamond grains and the metal-solvent catalyst of the at collectively exhibit a specific permeability of about 0.060 G·cm$^3$/g·Oe to about 0.090 G·cm$^3$/g·Oe; and
    wherein the polycrystalline diamond exhibits a G$_{ratio}$ of at least about 4.0×10$^6$.

2. The polycrystalline diamond of claim 1 wherein the coercivity is about 155 Oe to about 175 Oe.

3. The polycrystalline diamond of claim 1 wherein the coercivity is about 115 Oe to about 250 Oe.

4. The polycrystalline diamond of claim 1 wherein the coercivity is about 115 Oe to about 175 Oe.

5. The polycrystalline diamond of claim 1 wherein the specific magnetic saturation is about 5 G·cm$^3$/g to about 15 G·cm$^3$/g.

6. The polycrystalline diamond of claim 1 wherein the specific magnetic saturation is about 10 G·cm$^3$/g to about 15 G·cm$^3$/g.

7. The polycrystalline diamond of claim 1 wherein the coercivity is about 155 Oe to about 175 Oe, and the specific magnetic saturation is about 10 G·cm$^3$/g to about 15 G·cm$^3$/g.

8. The polycrystalline diamond of claim 1 wherein the plurality of diamond grains exhibit an average grain size of about 30 μm or less.

9. The polycrystalline diamond of claim 1 wherein the plurality of diamond grains exhibit an average grain size of about 20 μm or less.

10. The polycrystalline diamond of claim 1 wherein the metal-solvent catalyst is present in an amount of about 6 weight % or less, and comprises cobalt, iron, nickel, or alloys thereof.

11. The polycrystalline diamond of claim 1 wherein the amount of the metal-solvent catalyst is about 3 weight % to about 6 weight %.

12. The polycrystalline diamond of claim 1 wherein the amount of the metal-solvent catalyst is about 1 weight % to about 3 weight %.

13. The polycrystalline diamond of claim 1, further comprising a residual principal stress on a working surface thereof of about −345 MPa to about 0 MPa.

14. The polycrystalline diamond of claim 1 wherein the plurality of diamond grains and the metal-solvent catalyst define a volume of at least about 0.050 cm$^3$.

15. The polycrystalline diamond of claim 1 wherein the plurality of diamond grains and the metal-solvent catalyst define a volume of about 0.25 cm$^3$ to about 1.75 cm$^3$.

16. The polycrystalline diamond of claim 1 wherein the G$_{ratio}$ is about 8.0×10$^6$ to about 15.0×10$^6$.

17. The polycrystalline diamond of claim 1 in which a thermal stability thereof as determined by a distance cut, prior to failure, in a vertical lathe test is at least about 1300 m.

18. The polycrystalline diamond of claim 1 wherein the metal-solvent catalyst comprises at least about 50 weight % cobalt.

19. The polycrystalline diamond of claim 1 wherein the metal-solvent catalyst exhibits a specific magnetic saturation of about 185 G·cm$^3$/g to about 215 G·cm$^3$/g.

20. Polycrystalline diamond, comprising:
a plurality of diamond grains defining a plurality of interstitial regions;
a metal-solvent catalyst occupying a substantial number of the plurality of interstitial regions, the metal-solvent catalyst present in an amount of about 1 weight % to about 6 weight %;
wherein the plurality of diamond grains and the metal-solvent catalyst collectively coercivity is about 115 Oersteds ("Oe") to about 250 Oe;
wherein the plurality of diamond grains and the metal-solvent catalyst collectively exhibit a specific magnetic saturation of about 15 Gauss·cm$^3$/grams ("G·cm$^3$/g") or less;
wherein the plurality of diamond grains and the metal-solvent catalyst collectively define a volume of at least about 0.050 cm$^3$; and
wherein the polycrystalline diamond exhibits a $G_{ratio}$ of at least about $4.0 \times 10^6$.

21. The polycrystalline diamond of claim 20 wherein the volume is about 0.25 cm$^3$ to about 1.75 cm$^3$.

22. The polycrystalline diamond of claim 20 wherein the specific magnetic saturation is about 5 G·cm$^3$/g to about 15 G·cm$^3$/g.

23. The polycrystalline diamond of claim 20 wherein the specific magnetic saturation is about 10 G·cm$^3$/g to about 15 G·cm$^3$/g.

24. The polycrystalline diamond of claim 20 wherein the coercivity is about 155 Oe to about 175 Oe.

25. The polycrystalline diamond of claim 20 wherein the coercivity is about 115 Oe to about 175 Oe.

26. The polycrystalline diamond of claim 20 wherein the plurality of diamond grains and the metal-solvent catalyst collectively exhibit a specific permeability less than about 0.10.

27. The polycrystalline diamond of claim 20 wherein the plurality of diamond grains and the metal-solvent catalyst collectively exhibit a specific permeability of about 0.060 to about 0.090.

28. The polycrystalline diamond of claim 20 wherein the coercivity is about 155 Oe to about 175 Oe, and wherein the specific magnetic saturation is about 10 G·cm$^3$/g to about 15 G·cm$^3$/g.

29. The polycrystalline diamond of claim 20 wherein the plurality of diamond grains exhibit an average grain size of about 30 μm or less.

30. The polycrystalline diamond of claim 20 wherein the plurality of diamond grains exhibit an average grain size of about 20 μm or less.

31. The polycrystalline diamond of claim 20 wherein the metal-solvent catalyst is present in an amount of about 6 weight % or less, and further wherein the metal-solvent catalyst comprises cobalt, nickel, iron, or alloys thereof.

32. The polycrystalline diamond of claim 20 wherein the amount of the metal-solvent catalyst is about 3 weight % to about 6 weight %.

33. The polycrystalline diamond of claim 20 wherein the amount of the metal-solvent catalyst is about 1 weight % to about 3 weight %.

34. The polycrystalline diamond of claim 20, further comprising a residual principal stress on a working surface thereof of about −345 MPa to about 0 MPa.

35. The polycrystalline diamond of claim 20 wherein the $G_{ratio}$ is about $8.0 \times 10^6$ to about $15.0 \times 10^6$.

36. The polycrystalline diamond of claim 20 in which a thermal stability thereof as determined by a distance cut, prior to failure, in a vertical lathe test is at least about 1300 m.

37. The polycrystalline diamond of claim 20 wherein the metal-solvent catalyst comprises at least about 50 weight % cobalt.

38. The polycrystalline diamond of claim 20 wherein the metal-solvent catalyst exhibits a specific magnetic saturation of about 185 G·cm$^3$/g to about 215 G·cm$^3$/g.

39. Polycrystalline diamond, comprising:
a plurality of diamond grains defining a plurality of interstitial regions, the plurality of diamond grains exhibiting an average grain size of about 20 μm or less;
a metal-solvent catalyst occupying a substantial number of the plurality of interstitial regions, the metal-solvent catalyst present in an amount of about 1 weight % to about 6 weight %;
wherein the plurality of diamond grains and the metal-solvent catalyst collectively exhibit a coercivity of about 115 Oersteds ("Oe") or more;
wherein the plurality of diamond grains and the metal-solvent catalyst collectively exhibit a specific magnetic saturation of about 15 Gauss·cm$^3$/grams ("G·cm$^3$/g") or less indicative of the amount of metal-solvent catalyst;
wherein the plurality of diamond grains and the metal-solvent catalyst of the at collectively exhibit a specific permeability of less than about 0.10 G·cm$^3$/g·Oe; and
wherein the polycrystalline diamond exhibits a $G_{ratio}$ of at least about $4.0 \times 10^6$.

40. The polycrystalline diamond of claim 39 wherein the $G_{ratio}$ is about $8.0 \times 10^6$ to about $15.0 \times 10^6$.

41. The polycrystalline diamond of claim 39 wherein the $G_{ratio}$ is about $5.0 \times 10^6$ to about $15.0 \times 10^6$.

42. The polycrystalline diamond of claim 39 wherein the $G_{ratio}$ is at least about $30.0 \times 10^6$.

43. The polycrystalline diamond of claim 39 wherein the amount of the metal-solvent catalyst is about 1 weight % to about 3 weight %.

44. The polycrystalline diamond of claim 39 wherein the amount of the metal-solvent catalyst is about 3 weight % to about 6 weight %.

45. The polycrystalline diamond of claim 39 wherein the $G_{ratio}$ is at least about $30.0 \times 10^6$.

46. The polycrystalline diamond of claim 39 wherein the average grain size of the plurality of diamond grains is about 10 μm to about 18 μm.

47. The polycrystalline diamond of claim 39 wherein the average grain size of the plurality of diamond grains is about 15 μm to about 18 μm.

48. The polycrystalline diamond of claim 39 wherein the average grain size of the plurality of diamond grains is about 10 μm or less.

49. The polycrystalline diamond of claim 39 wherein the amount of the metal-solvent catalyst is about 3 weight % to about 6 weight %, and wherein the plurality of diamond grains and the metal-solvent catalyst defines a volume of about 0.25 cm$^3$ to about 1.75 cm$^3$.

50. The polycrystalline diamond of claim 49, further comprising an additional plurality of diamond grains defining a plurality of additional interstitial regions from which the metal-solvent catalyst has been at least partially leached.

51. The polycrystalline diamond of claim 50 wherein the polycrystalline diamond is substantially cylindrical and exhibits a diameter of about 0.8 centimeters to about 3 centimeters.

52. The polycrystalline diamond of claim 51 further comprising a chamfer formed between an upper surface and a side surface.

53. The polycrystalline diamond of claim 7 further comprising an additional plurality of diamond grains defining a plurality of additional interstitial regions from which the metal-solvent catalyst has been at least partially leached.

54. The polycrystalline diamond of claim 53 wherein the polycrystalline diamond is substantially cylindrical and exhibits a diameter of about 0.8 centimeters to about 3 centimeters.

55. The polycrystalline diamond of claim 54 further comprising a chamfer formed between an upper surface and a side surface.

56. The polycrystalline diamond of claim 1 further comprising an additional plurality of diamond grains defining a plurality of additional interstitial regions from which the metal-solvent catalyst has been at least partially leached.

57. The polycrystalline diamond of claim 1 wherein the $G_{ratio}$ is at least about $30.0 \times 10^6$.

58. The polycrystalline diamond of claim 28 further comprising an additional plurality of diamond grains defining a plurality of additional interstitial regions from which the metal-solvent catalyst has been at least partially leached.

59. The polycrystalline diamond of claim 58 wherein the polycrystalline diamond is substantially cylindrical and exhibits a diameter of about 0.8 centimeters to about 3 centimeters.

60. The polycrystalline diamond of claim 21 further comprising an additional plurality of diamond grains defining a plurality of additional interstitial regions from which the metal-solvent catalyst has been at least partially leached.

61. The polycrystalline diamond of claim 60 wherein the polycrystalline diamond is substantially cylindrical and exhibits a diameter of about 0.8 centimeters to about 3 centimeters.

62. The polycrystalline diamond of claim 61 further comprising a chamfer formed between an upper surface and a side surface.

\* \* \* \* \*

UNITED STATES PATENT AND TRADEMARK OFFICE
CERTIFICATE OF CORRECTION

| | |
|---|---|
| PATENT NO. | : 8,158,258 B2 |
| APPLICATION NO. | : 12/846604 |
| DATED | : April 17, 2012 |
| INVENTOR(S) | : Bertagnolli et al. |

Page 1 of 1

It is certified that error appears in the above-identified patent and that said Letters Patent is hereby corrected as shown below:

IN THE CLAIMS:

Column 18
In Claim 1, Line 21, change "catalyst of the at collectively" to --catalyst collectively--

Column 20
In Claim 39, Line 34, change "catalyst of the at collectively" to --catalyst collectively--

Signed and Sealed this
Twenty-sixth Day of March, 2013

Teresa Stanek Rea
*Acting Director of the United States Patent and Trademark Office*